(12) United States Patent
Hsiao et al.

(10) Patent No.: US 12,405,283 B1
(45) Date of Patent: Sep. 2, 2025

(54) HLAB AUTOMATION AND RELATED SYSTEMS AND METHODS

(71) Applicant: Hyperius Biotech Inc., Wellesley, MA (US)

(72) Inventors: Yu-Shun Hsiao, Wellesley, MA (US); Yen-Po Chin, Taipei (TW)

(73) Assignee: Hyperius Biotech Inc, Wellesley, MA (US)

( * ) Notice: Subject to any disclaimer, the term of this patent is extended or adjusted under 35 U.S.C. 154(b) by 0 days.

(21) Appl. No.: 18/807,867

(22) Filed: Aug. 16, 2024

(51) Int. Cl.
| | | |
|---|---|---|
| *G01N 35/02* | (2006.01) | |
| *B01L 1/00* | (2006.01) | |
| *B25J 9/16* | (2006.01) | |
| *C12M 1/00* | (2006.01) | |
| *C12M 1/26* | (2006.01) | |
| *C12M 1/36* | (2006.01) | |
| *G01N 35/00* | (2006.01) | |
| *G05D 1/246* | (2024.01) | |
| *G05D 1/656* | (2024.01) | |
| *G05D 105/80* | (2024.01) | |
| *G05D 107/00* | (2024.01) | |

(52) U.S. Cl.
CPC ............... *G01N 35/02* (2013.01); *B01L 1/00* (2013.01); *B25J 9/1679* (2013.01); *B25J 9/1697* (2013.01); *C12M 33/04* (2013.01); *C12M 41/14* (2013.01); *C12M 41/48* (2013.01); *G01N 35/00722* (2013.01); *G05D 1/2465* (2024.01); *G05D 1/656* (2024.01); *G01N 2035/00891* (2013.01); *G05D 2105/80* (2024.01); *G05D 2107/68* (2024.01)

(58) Field of Classification Search
CPC ............ G01N 35/02; G01N 35/00722; G01N 2035/00891; B01L 1/00; B25J 9/1679; B25J 9/1697; C12M 33/04; C12M 41/14; C12M 41/48; G05D 1/2465; G05D 1/656; G05D 2105/80; G05D 2107/68
See application file for complete search history.

(56) References Cited

U.S. PATENT DOCUMENTS

| | | |
|---|---|---|
| 9,845,167 B1 | 12/2017 | Parietti et al. |
| 10,456,975 B2 | 10/2019 | Parietti et al. |
| 10,773,392 B2 | 9/2020 | Bright et al. |
| 11,142,353 B2 | 10/2021 | Parietti et al. |
| 11,198,845 B2 | 12/2021 | Scarfogliero et al. |
| 11,505,776 B2 | 11/2022 | Veraitch et al. |
| 11,955,873 B2 | 4/2024 | Gandolfi et al. |
| 11,993,765 B2 | 5/2024 | Veraitch et al. |
| 2017/0217027 A1* | 8/2017 | Boucard ................ B25J 19/023 |

(Continued)

FOREIGN PATENT DOCUMENTS

| | | |
|---|---|---|
| GB | 2301148 A | 11/1996 |
| GB | 2307962 A | 6/1997 |

(Continued)

*Primary Examiner* — Basil T. Jos
(74) *Attorney, Agent, or Firm* — Procopio, Cory, Hargreaves & Savitch LLP

(57) ABSTRACT

The present disclosure relates to a system that comprises a lab space housing multiple workstations comprising at least two workstations each performing a different type of bio lab task from another. The lab space can have a lab floor space comprising an occupied lab floor space on which the multiple workstations are occupied, and an unoccupied lab floor space on which a stand-alone robotic arm moves through.

19 Claims, 7 Drawing Sheets

(56) References Cited

U.S. PATENT DOCUMENTS

| | | | |
|---|---|---|---|
| 2018/0290311 A1 | 10/2018 | Chandra et al. | |
| 2019/0016048 A1 | 1/2019 | Rutter et al. | |
| 2019/0061143 A1 | 2/2019 | Chandra et al. | |
| 2020/0255790 A1 | 8/2020 | Veraitch et al. | |
| 2022/0119749 A1 | 4/2022 | Stone et al. | |
| 2022/0325219 A1 | 10/2022 | Scarfogliero et al. | |
| 2023/0019545 A1 | 1/2023 | Veraitch et al. | |
| 2023/0098602 A1* | 3/2023 | Cella | B25J 9/1674 700/248 |
| 2023/0102750 A1 | 3/2023 | Parietti et al. | |
| 2023/0167393 A1 | 6/2023 | Veraitch et al. | |
| 2023/0203419 A1 | 6/2023 | Strange et al. | |
| 2023/0228784 A1 | 7/2023 | Kreciglowa et al. | |
| 2023/0365911 A1 | 11/2023 | Ainane et al. | |
| 2024/0009136 A1 | 1/2024 | Parietti et al. | |
| 2024/0182844 A1 | 6/2024 | Mason et al. | |

FOREIGN PATENT DOCUMENTS

| | | |
|---|---|---|
| GB | 2311394 A | 9/1997 |
| GB | 2312380 A | 10/1997 |
| GB | 2605860 A | 10/2022 |
| GB | 2614464 A | 7/2023 |
| GB | 2614465 A | 7/2023 |
| WO | 2018014030 A1 | 1/2018 |
| WO | 2018232411 A1 | 12/2018 |
| WO | 2021144560 A1 | 7/2021 |
| WO | 2021212124 A1 | 10/2021 |
| WO | 2022269231 A1 | 12/2022 |
| WO | 2023007155 A1 | 2/2023 |
| WO | 2023012469 A1 | 2/2023 |
| WO | 2023017260 A1 | 2/2023 |
| WO | 2023037086 A1 | 3/2023 |
| WO | 2023047115 A1 | 3/2023 |
| WO | 2023094794 A1 | 6/2023 |
| WO | 2023139383 A1 | 7/2023 |
| WO | 2023148496 A1 | 8/2023 |
| WO | 2023161615 A1 | 8/2023 |
| WO | 2023170387 A1 | 9/2023 |
| WO | 2023187414 A1 | 10/2023 |
| WO | 2024038280 A1 | 2/2024 |
| WO | 2024047357 A2 | 3/2024 |
| WO | 2024047361 A2 | 3/2024 |
| WO | 2024074838 A2 | 4/2024 |
| WO | 2024110748 A2 | 5/2024 |

* cited by examiner

HLAB AUTOMATION AND RELATED SYSTEMS AND METHODS

BACKGROUND

Laboratory work can be a fundamental aspect of scientific research and experimentation across various disciplines such as biology, chemistry, physics, engineering, and medicine. It involves conducting experiments, gathering data, and analyzing results in a controlled environment to test hypotheses, validate theories, and advance knowledge in the respective fields. With the advancement of science and technology, lab and preparatory work involving reagents and cleaning solutions in biology, chemistry, and other laboratory settings is increasingly recognized.

SUMMARY

This Summary is provided to introduce a selection of concepts in simplified form that can be further described below in the Detailed Description. This Summary is not intended to identify key aspects or essential aspects of the claimed subject matter.

All features of exemplary embodiments which can be described in this disclosure and can be not mutually exclusive can be combined with one another. Elements of one embodiment can be utilized in the other embodiments without further mention. Other aspects and features of the present invention will become apparent to those ordinarily skilled in the art upon review of the following description of specific embodiments in conjunction with any accompanying Figures.

The present disclosure relates to a system including a lab space housing multiple workstations including at least two workstations each performing a different type of bio lab task from another, wherein the lab space has a lab floor space including an occupied lab floor space on which the multiple workstations are occupied, and an unoccupied lab floor space on which a stand-alone robotic arm moves through, wherein the stand-alone robotic arm includes visual assistance to determine a move path on the unoccupied lab floor space for the stand-alone robotic arm to move to or among the multiple workstations, and wherein the visual assistance assists the stand-alone robotic arm to be positioned at each of the multiple workstations depending on the bio lab task to be performed.

In some embodiments, the stand-alone robotic arm is not attached to any of the multiple workstations.

In some embodiments, the visual assistance visualizes the path and modify the path depending on the relative positions or the shapes of the multiple workstations.

In some embodiments, no more than about 80% of the lab floor space is unoccupied. In some embodiments, no more than about 70% of the lab floor space is unoccupied.

In some embodiments, the stand-alone robotic arm includes a controller that controls the movement of the stand-alone robotic arm to perform tasks on multiple workstations, and wherein visualization assistance is operationally associated with the controller to assist the stand-alone robotic arm to perform tasks.

In some embodiments, visualization assistance visualizes a functional object on the workstation and assists the stand-alone robotic arm to move toward and manipulate the functional object.

In some embodiments, visualization assistance visualizes a functional object on the workstation and assists the stand-alone robotic arm to contact the functional object.

In some embodiments, the stand-alone robotic arm includes a controller that controls the movement of the stand-alone robotic arm to perform tasks on multiple workstations, and wherein visualization assistance is operationally associated with the controller to assist the stand-alone robotic arm to move toward and manipulate the functional object.

In some embodiments, the stand-alone robotic arm includes a controller that controls the movement of the stand-alone robotic arm to perform tasks on multiple workstations, and wherein visualization assistance is operationally associated with the controller to assist the stand-alone robotic arm to contact the functional object.

In some embodiments, the visualization assistance further visualizes the failure of moving toward the functional object and inform the controller to adjust the movement of the stand-alone robotic arm.

In some embodiments, the visualization assistance further visualizes a failure of manipulating the functional object and inform the controller to adjust the movement of the stand-alone robotic arm to adjust manipulating the functional object.

In some embodiments, the visualization assistance further visualizes a failure of going around an object and inform the controller to adjust the movement of the stand-alone robotic arm to adjust manipulating the functional object.

In some embodiments, the visualization assistance further visualizes a failure of manipulating the functional object and inform the controller to adjust the movement of the stand-alone robotic arm to adjust manipulating the functional object.

In some embodiments, the visualization assistance further visualizes a failure of contacting the functional object and inform the controller to adjust the movement of the stand-alone robotic arm to adjust contacting the functional object.

In some embodiments, the visualization assistance further visualizes a failure of actuating the switch on the functional object and inform the controller to adjust the movement of the stand-alone robotic arm to adjust actuating the switch the functional object.

In some embodiments, the visualization assistance further visualizes a failure of touching the touch screen from one location to another and inform the controller to adjust the movement of the stand-alone robotic arm to adjust touching the touch screen.

In some embodiments, the visualization assistance includes a sensor.

In some embodiments, the multiple workstations include a patient tissue processing station, a cell enrichment station, a cell activation or cell transduction station, a cell proliferation or expansion station, a cell enrichment station, a cell purification and formulation station, a cell cryopreservation station, or a combination thereof.

In some embodiments, the system operates based on a computer-implemented method including: obtaining a three dimensional map of a bio lab environment; assigning locations of the multiple workstations for interactions by the stand-alone robotic arm; generating a plurality of waypoints corresponding to the multiple workstations, using a machine learning model and based on the three dimensional map of the bio lab environment and the locations of the multiple workstations the interaction point; generating operation data from monitoring operation of the robotic device to control the multiple workstations operated based on the plurality of waypoints; and feeding back the generated operation data to the machine learning model to generate an updated plurality of waypoints corresponding to the multiple workstations.

These and other objects, features, and characteristics of the system and/or method disclosed herein, as well as the methods of operation and functions of the related elements of structure and the combination of parts and economies of manufacture, will become more apparent upon consideration of the following description and the appended claims with reference to the accompanying drawings, all of which form a part of this specification.

BRIEF DESCRIPTION OF THE DRAWING

It is to be expressly understood that the drawings are for the purpose of illustration and description only and are not intended as a definition of the limits of the invention.

DETAILED DESCRIPTION

Figure 1:
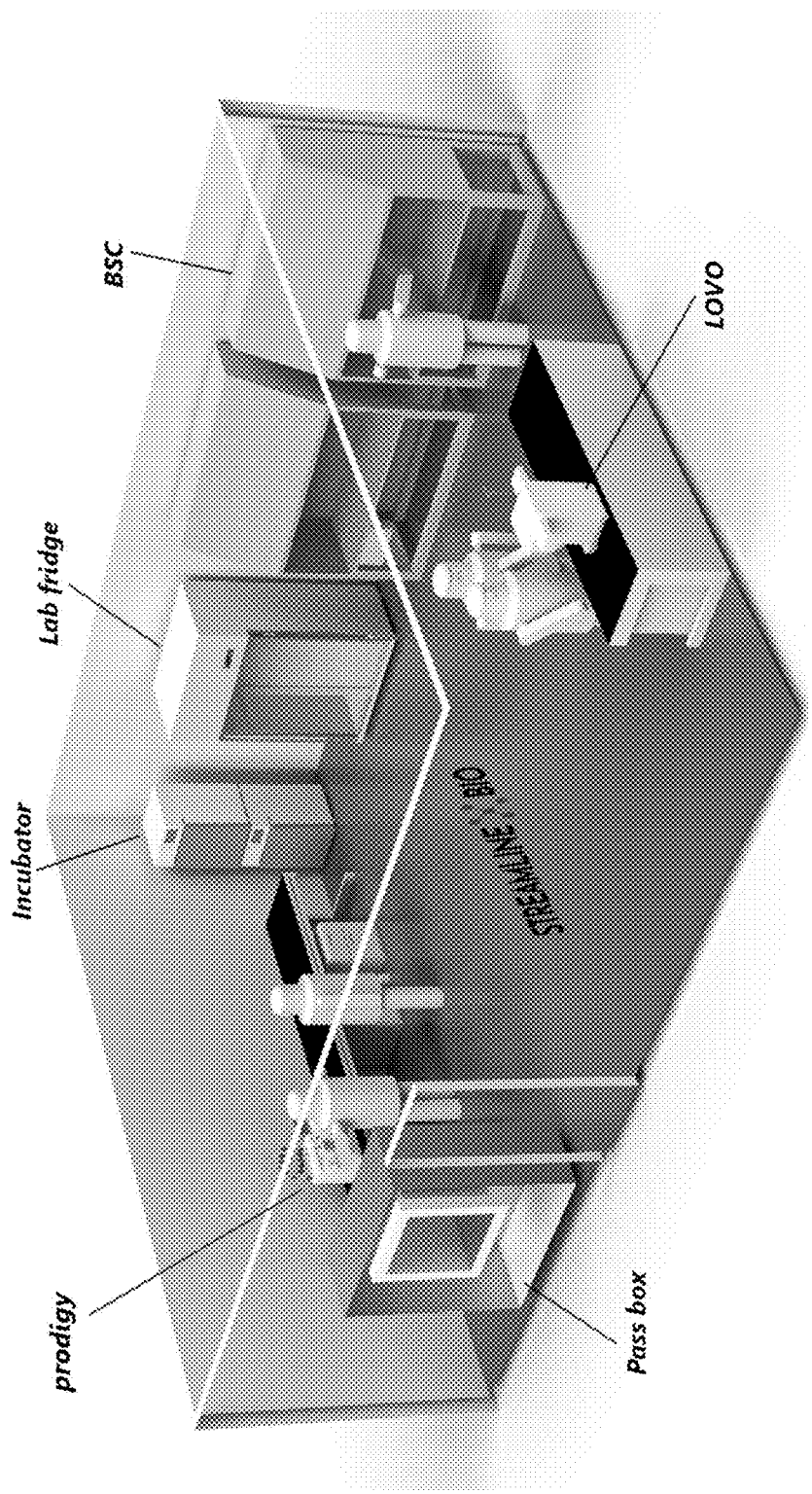
FIG. 1 illustrates an example lab system involving a plurality of human laboratory workers or technicians that are generally and currently implemented in some embodiments.

Hereinafter, the present disclosure will be described in detail. Prior to the description, it should be understood that the terms or words used in the specification and the appended claims should not be construed as limited to general and dictionary meanings, but rather interpreted based on the meanings and concepts corresponding to the technical aspects of the present disclosure on the basis of the principle that the inventor is allowed to define terms appropriately for the best explanation. Therefore, the embodiments described herein and the elements shown in the drawings is just a most preferred embodiment of the present disclosure, but not intended to fully describe the technical aspects of the present disclosure, so it should be understood that other equivalents and modifications could have been made thereto at the time the application was filed.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The terms "about" and "essentially" are used herein in the sense of at, or nearly at, when given the manufacturing and material tolerances inherent in the stated circumstances and are used to prevent the unscrupulous infringer from unfairly taking advantage of the present disclosure where exact or absolute figures are stated as an aid to understanding the present disclosure.

"A and/or B" when used in this specification, specifies "either A or B or both".

As used herein, the terms proximal and distal in the context of the apparatus refer to proximal and distal as referenced from the apparatus outside an object, such that proximal may refer to components outside the object and distal may refer to components inside the object or attached to the object, or on a surface of the object.

The present disclosure recognizes that there's a growing demand for precision and speed in preparing and conducting lab work.

In some embodiments, the maintenance of the controlled environment may demand care and labor when handling samples. With the advancement of science and technology, the significance of preparatory work involving reagents and cleaning solutions in biology, chemistry, and other laboratory settings is increasingly recognized. Consequently, there's a growing demand for precision and speed in in laboratory work such as preparing and replacing solutions.

In some embodiments, an automated system or solution for laboratory work can be provided. In some embodiments, automating the entire bio or chemistry lab such as a cell culture process including, cell isolation or purification, cell proliferation, and preservation, and aiming to reduce manual labor in a laboratory or a factory can be provided.

In some embodiments, AI-based feedback check can be implemented. In some embodiments, AI image analysis will be employed to perform the precision of the bag replacement process and to provide real-time system feedback. In some embodiments, a database to log operational data for monitoring and improving system performance can be implemented.

The present disclosure relates to a system including a lab space housing multiple workstations including at least two workstations each performing a different type of bio lab task from another, wherein the lab space has a lab floor space including an occupied lab floor space on which the multiple workstations are occupied, and an unoccupied lab floor space on which a stand-alone robotic arm moves through, wherein the stand-alone robotic arm includes visual assistance to determine a move path on the unoccupied lab floor space for the stand-alone robotic arm to move to or among the multiple workstations, and wherein the visual assistance assists the stand-alone robotic arm to be positioned at each of the multiple workstations depending on the bio lab task to be performed.

In some embodiments, the stand-alone robotic arm is not attached to any of the multiple workstations.

In some embodiments, the lab floor space does not include a track on which robotic arm moves. In some embodiments, the lab floor space includes a track on which robotic arm moves.

In some embodiments, the visual assistance visualizes the path and modify the path depending on the relative positions of the multiple workstations. In some embodiments, the visual assistance visualizes the path and modify the path depending on the shapes of the multiple workstations. In some embodiments, the visual assistance visualizes the path and modify the path depending on the relative positions of obstacles unrelated to the multiple workstations.

In some embodiments, no more than about 80% of the lab floor space is unoccupied. In some embodiments, no more than about 75% of the lab floor space is unoccupied. In some embodiments, no more than about 70% of the lab floor space is unoccupied. In some embodiments, no more than about 65% of the lab floor space is unoccupied. In some embodiments, no more than about 60% of the lab floor space is unoccupied. In some embodiments, no more than about 55% of the lab floor space is unoccupied. In some embodiments, no more than about 50% of the lab floor space is unoccupied. In some embodiments, no more than about 45% of the lab floor space is unoccupied. In some embodiments, no more than about 40% of the lab floor space is unoccupied. In some embodiments, no more than about 35% of the lab floor space is unoccupied. In some embodiments, no more than about 30% of the lab floor space is unoccupied. In some embodiments, no more than about 25% of the lab floor space is unoccupied. In some embodiments, no more than about 20% of the lab floor space is unoccupied. In some embodiments, no more than about 15% of the lab floor space is unoccupied. In some embodiments, no more than about 10% of the lab floor space is unoccupied. In some embodiments, no more than about 5% of the lab floor space is unoccupied.

In some embodiments, the stand-alone robotic arm increases a process time of the system based on the multiple workstations by at least about 2 times. In some embodiments, the stand-alone robotic arm increases a process time of the system based on the multiple workstations by at least about 3 times. In some embodiments, the stand-alone robotic arm increases a process time of the system based on the multiple workstations by at least about 5 times. In some embodiments, the stand-alone robotic arm increases a process time of the system based on the multiple workstations by at least about 10 times. In some embodiments, the stand-alone robotic arm increases a process time of the system based on the multiple workstations by at least about 15 times. In some embodiments, the stand-alone robotic arm increases a process time of the system based on the multiple workstations by at least about 20 times. In some embodiments, the stand-alone robotic arm increases a process time of the system based on the multiple workstations by at least about 30 times. In some embodiments, the stand-alone robotic arm increases a process time of the system based on the multiple workstations by at least about 40 times. In some embodiments, the stand-alone robotic arm increases a process time of the system based on the multiple workstations by at least about 50 times. In some embodiments, the stand-alone robotic arm increases a process time of the system based on the multiple workstations by at least about 60 times. In some embodiments, the stand-alone robotic arm increases a process time of the system based on the multiple workstations by at least about 62 times.

In some embodiments, the stand-alone robotic arm includes a controller that controls the movement of the stand-alone robotic arm to perform tasks on multiple workstations, and wherein visualization assistance is operationally associated with the controller to assist the stand-alone robotic arm to perform tasks. In some embodiments, visualization assistance visualizes a functional object on the workstation and assists the stand-alone robotic arm to move toward and manipulate the functional object. In some embodiments, visualization assistance visualizes a functional object on the workstation and assists the stand-alone robotic arm to grab the functional object. In some embodiments, visualization assistance visualizes a functional object on the workstation and assists the stand-alone robotic arm to contact the functional object. In some embodiments, visualization assistance visualizes a functional object on the workstation and assists the stand-alone robotic arm to transfer the functional object from one location to another location. In some embodiments, visualization assistance visualizes a functional object on the workstation and assists the stand-alone robotic arm to rub the functional object. In some embodiments, visualization assistance visualizes a functional object on the workstation and assists the stand-alone robotic arm to actuate a switch on the functional object. In some embodiments, visualization assistance visualizes a functional object on the workstation and assists the stand-alone robotic arm to push a button on a functional object. In some embodiments, visualization assistance visualizes a functional object on the workstation and assists the stand-alone robotic arm to touch a touch screen.

In some embodiments, the stand-alone robotic arm includes a controller that controls the movement of the stand-alone robotic arm to perform tasks on multiple workstations, and wherein visualization assistance is operationally associated with the controller to assist the stand-alone robotic arm to move toward and manipulate the functional object. In some embodiments, the stand-alone robotic arm includes a controller that controls the movement of the stand-alone robotic arm to perform tasks on multiple workstations, and wherein visualization assistance is operationally associated with the controller to assist the stand-alone robotic arm to grab the functional object. In some embodiments, the stand-alone robotic arm includes a controller that controls the movement of the stand-alone robotic arm to perform tasks on multiple workstations, and wherein visualization assistance is operationally associated with the controller to assist the stand-alone robotic arm to contact the functional object. In some embodiments, the stand-alone robotic arm includes a controller that controls the movement of the stand-alone robotic arm to perform tasks on multiple workstations, and wherein visualization assistance is operationally associated with the controller to assist the stand-alone robotic arm to transfer the functional object from one location to another location. In some embodiments, the stand-alone robotic arm includes a controller that controls the movement of the stand-alone robotic arm to perform tasks on multiple workstations, and wherein visualization assistance is operationally associated with the controller to assist the stand-alone robotic arm to rub the functional object. In some embodiments, the stand-alone robotic arm includes a controller that controls the movement of the stand-alone robotic arm to perform tasks on multiple workstations, and wherein visualization assistance is operationally associated with the controller to assist the stand-alone robotic arm to actuate a switch on the functional object. In some embodiments, the stand-alone robotic arm includes a controller that controls the movement of the stand-alone robotic arm to perform tasks on multiple workstations, and wherein visualization assistance is operationally associated with the controller to assist the stand-alone robotic arm to push a button on a functional object. In some embodiments, the stand-alone robotic arm includes a controller that controls the movement of the stand-alone robotic arm to perform tasks on multiple workstations, and wherein visualization assistance is operationally associated with the controller to assist the stand-alone robotic arm to touch a touch screen.

In some embodiments, the visualization assistance further visualizes the failure of moving toward the functional object and inform the controller to adjust the movement of the stand-alone robotic arm. In some embodiments, the visualization assistance further visualizes a failure of manipulating the functional object and inform the controller to adjust the movement of the stand-alone robotic arm to adjust manipulating the functional object. In some embodiments, the visualization assistance further visualizes an obstructing object obstructing the stand-alone robotic arm from manipulating the functional object and inform the controller to adjust the movement of the stand-alone robotic arm to adjust manipulating the functional object. In some embodiments, the visualization assistance further visualizes a failure of going around an object and inform the controller to adjust the movement of the stand-alone robotic arm to adjust manipulating the functional object. In some embodiments, the visualization assistance further visualizes a failure of manipulating the functional object and inform the controller to adjust the movement of the stand-alone robotic arm to adjust manipulating the functional object. In some embodiments, the visualization assistance further visualizes a failure of grabbing the functional object and inform the controller to adjust the movement of the stand-alone robotic arm to adjust grabbing the functional object. In some embodiments, the visualization assistance further visualizes a failure of contacting the functional object and inform the controller to adjust the movement of the stand-alone robotic arm to adjust contacting the functional object. In some embodiments, the visualization assistance further visualizes a failure of transferring the functional object from one location to another and inform the controller to adjust the movement of the stand-alone robotic arm to adjust transferring the functional object. In some embodiments, the visualization assistance further visualizes a failure of rubbing the functional object and inform the controller to adjust the movement of the stand-alone robotic arm to adjust rubbing the functional object. In some embodiments, the visualization assistance further visualizes a failure of actuating the switch on the functional object and inform the controller to adjust the movement of the stand-alone robotic arm to adjust actuating the switch the functional object. In some embodiments, the visualization assistance further visualizes a failure of touching the touch screen from one location to another and inform the controller to adjust the movement of the stand-alone robotic arm to adjust touching the touch screen.

In some embodiments, the visualization assistance includes a sensor. In some embodiments, the visualization assistance includes a 3D sensor. In some embodiments, the visualization assistance includes a camera. In some embodiments, the visualization assistance includes a 3D camera. In some embodiments, the visualization assistance includes a LiDAR sensor. In some embodiments, the visualization assistance includes a laser sensor. In some embodiments, the visualization assistance includes a UV light sensor. In some embodiments, the visualization assistance includes an infrared sensor. In some embodiments, the visualization assistance includes a point cloud sensor. In some embodiments, the visualization assistance includes a laser scanning sensor. In some embodiments, the visualization assistance includes an electromagnetic wave scanner. In some embodiments, the visualization assistance includes a Time-of-Flight (ToF) Sensor. In some embodiments, the visualization assistance includes a Dual lens camera. In some embodiments, the visualization assistance includes a structured-light 3D scanner.

In some embodiments, the multiple workstations include a patient tissue processing station. In some embodiments, the multiple workstations include a cell enrichment station. In some embodiments, the multiple workstations include a cell activation and/or cell transduction station. In some embodiments, the multiple workstations include a cell proliferation or expansion station. In some embodiments, the multiple workstations include a cell enrichment station. In some embodiments, the multiple workstations include a cell purification and formulation station. In some embodiments, the multiple workstations includes a cell cryopreservation station. In some embodiments, the multiple workstations includes a pre-process station.

In some embodiments, the multiple workstations includes a station to perform homogenization, isolation, washing, removal, depletion, separation, filtration, pre-treatment, enzymatic treatment, selection, or cryopreservation, or any combination thereof. In some embodiments, the multiple workstations includes a cell selection station. In some embodiments, the multiple workstations includes a station to perform enrichment, isolation, separation, purification, collection, sorting, cumulating, capture, depletion, removal, separation, or any combination thereof. In some embodiments, the multiple workstations includes a non-genetic manipulation station. In some embodiments, the multiple workstations includes a non-genetic manipulation station to perform activation, stimulation, enhancing, promotion, booster, seeding, inoculation, recovery, attachment, or any combination thereof. In some embodiments, the multiple workstations includes a gene modification station. In some embodiments, the multiple workstations includes a station to perform transduction, electroporation, nucleofection, transfection, modification, delivery, genetic engineering, genetic editing, cell squeezing, infusion, microinjection, cargo loading, or any combination thereof. In some embodiments, the multiple workstations includes a expansion station. In some embodiments, the multiple workstations includes a station to perform proliferation, culture, production, growth, or any combination thereof. In some embodiments, the multiple workstations includes a formulation and filling station. In some embodiments, the multiple workstations includes a station to perform reconstitution, concentration, aliquot, or any combination thereof. In some embodiments, the multiple workstations includes a cryopreservation station. In some embodiments, the multiple workstations includes a station to perform cell freezing.

In some embodiments, the system operates based on a computer-implemented method including: obtaining a three dimensional map of a bio lab environment; assigning locations of the multiple workstations for interactions by the stand-alone robotic arm; generating a plurality of waypoints corresponding to the multiple workstations, using a machine learning model and based on the three dimensional map of the bio lab environment and the locations of the multiple workstations the interaction point; generating operation data from monitoring operation of the robotic device to control the multiple workstations operated based on the plurality of waypoints; and feeding back the generated operation data to the machine learning model to generate an updated plurality of waypoints corresponding to the multiple workstations.

In some embodiments, localization can be performed to localize a machine or a conduct unit operation for a machine, wherein the localization can be any perception in general, which may include computer imaging, computer vision, sensing, sound and other medium for perception.

FIG. 1 illustrates an example lab system involving a plurality of human laboratory workers or technicians that are generally or currently implemented in some embodiments. Referring to FIG. 1, the example laboratory system requires relatively mostly empty floor space for the human laboratory workers to move around to perform their tasks. Moreover, this floor space often needs to be merged to provide mostly common spaces, which could additionally limit the allocating other lab equipment. These requirements with a plurality of human workers often demand more floor spaces, which can be more than about 75 square meters or about 800 square feet. The number of technicians required to perform the tasks could be 5 people at a time. The processes and tasks performed by human workers can be relatively manual, expensive and low-throughput processes.

Figure 2:
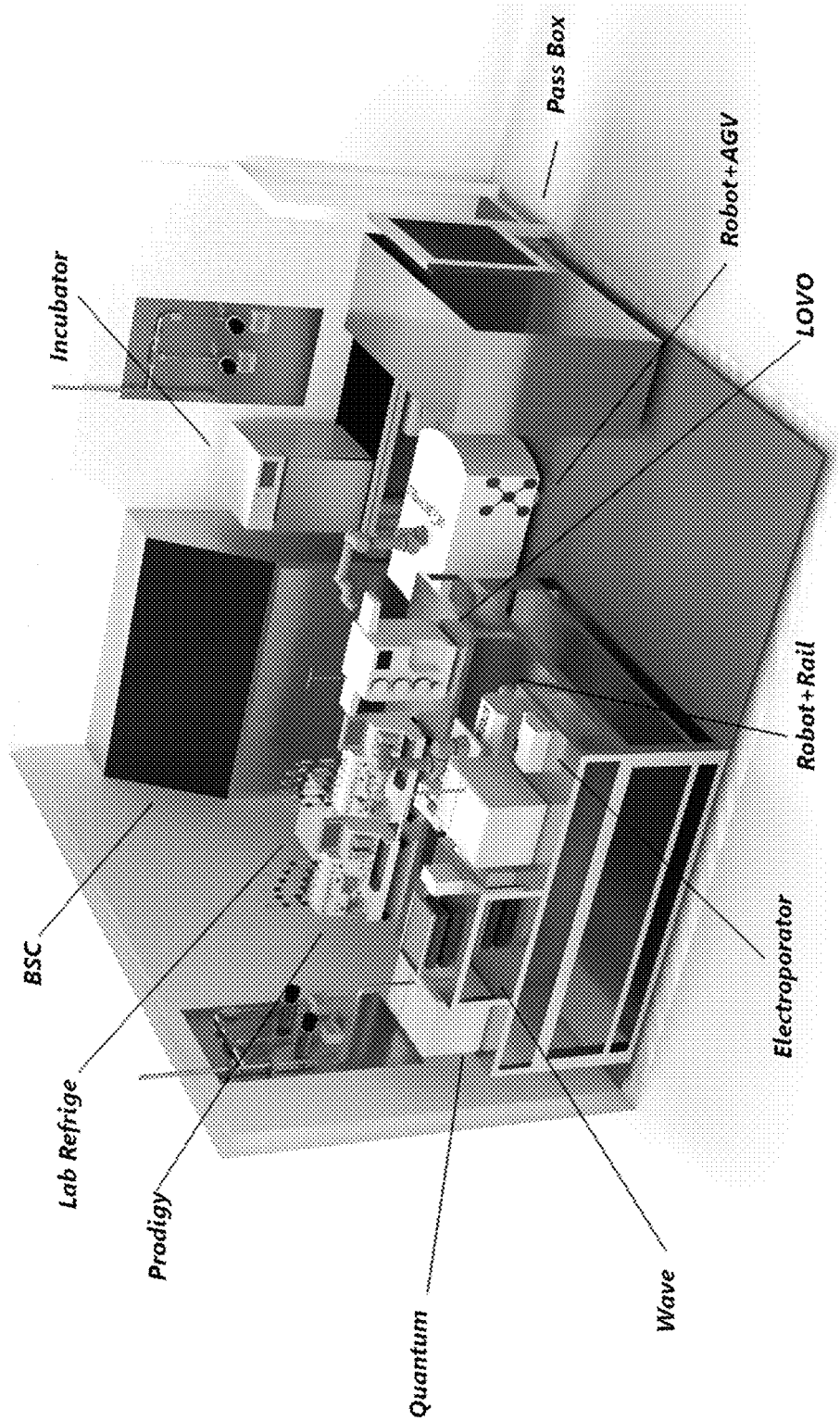
FIG. 2 illustrates an example artificial intelligence-based laboratory system that is at least substantially automated in some embodiments.

FIG. 2 illustrates an example artificial intelligence-based laboratory system that is at least substantially automated in some embodiments. Referring to FIG. 2, an example artificial intelligence-based laboratory system with a moving device such as a robotic arm with mobility can perform the processes or tasks that would require a plurality of human laboratory workers. The multi-functionality and mobility of the moving device requires substantially less floor space to perform the process or task that would require a plurality of human laboratory workers. For example, the floor space required can be about 25 square meter or about 270 square feet. Moreover, the number of human workers can be reduced, such a zero human workers. More number of workstations or laboratory devices can be fit in. Referring to FIG. 2, two CliniMACS Prodigy Platform, two Quantum, two Lovo, and 2 Wave were placed in the system, compared to one CliniMACS Prodigy Platform and one Lovo placed in FIG. 1. In some embodiments, artificial intelligence controlled robotic systems with real-time vision and motion planning in a human-free environment can be implemented. In some embodiments, the automation according to the present disclosure enables up to about 62 times faster motion planning than traditional laboratory performance by human workers, which can maximize cell viability or chemical stability by minimizing transition times such as cell transition time.

In some embodiment, an artificial intelligence controlled robotic system can scale up a corresponding operations such as a lab work and cell growth lab operations, e.g., due to the possibility of adding in a plurality of robotic system, which can be identical, similar, or different types of robotic systems. In comparison to scaling up conventional manufacturing and lab involving human workers with significantly more space and human resources requirements, operations based on an artificial intelligence controlled robotic system can be scaled up relatively more efficiently, for example, in terms of time and resources requirements. In some embodiments, using AI automation in manufacturing, bio labs, and cell growth labs can enhance efficiency, accuracy, and productivity. In some embodiments, maintenance of the operations can be more predictive. In some embodiments, AI algorithms can analyze data from machinery and equipment to predict maintenance needs before failures occur. In some embodiments, scaling up prevent costly downtime and extends equipment life, supporting larger production volumes with fewer disruptions. In some embodiments, AI-driven vision systems inspect products for defects and inconsistencies, can enhance the consistency and reliability of quality checks, ensuring high standards are maintained as production scales, or can increase production speed and consistency, enabling higher output without proportional increases in labor costs. In some embodiments, scaling up can streamline operations and reduces costs, supporting the efficient scaling of production processes. In some embodiments, in bio laboratory settings, scaling up can increase throughput and consistency, allowing bio labs to manage larger volumes of samples efficiently. In some embodiments, A scaled up AI-based robotics systems can monitor cell cultures in substantially real-time, assessing parameters such as growth and viability and can ensure optimal conditions for larger-scale cell cultures and improves consistency across multiple cultures. In some embodiments, AI-based system can automate the screening of compounds or conditions affecting cell growth. In some embodiments, scaling up can speed up the screening process, enabling the evaluation of larger numbers of compounds or conditions more efficiently.

Figure 3:
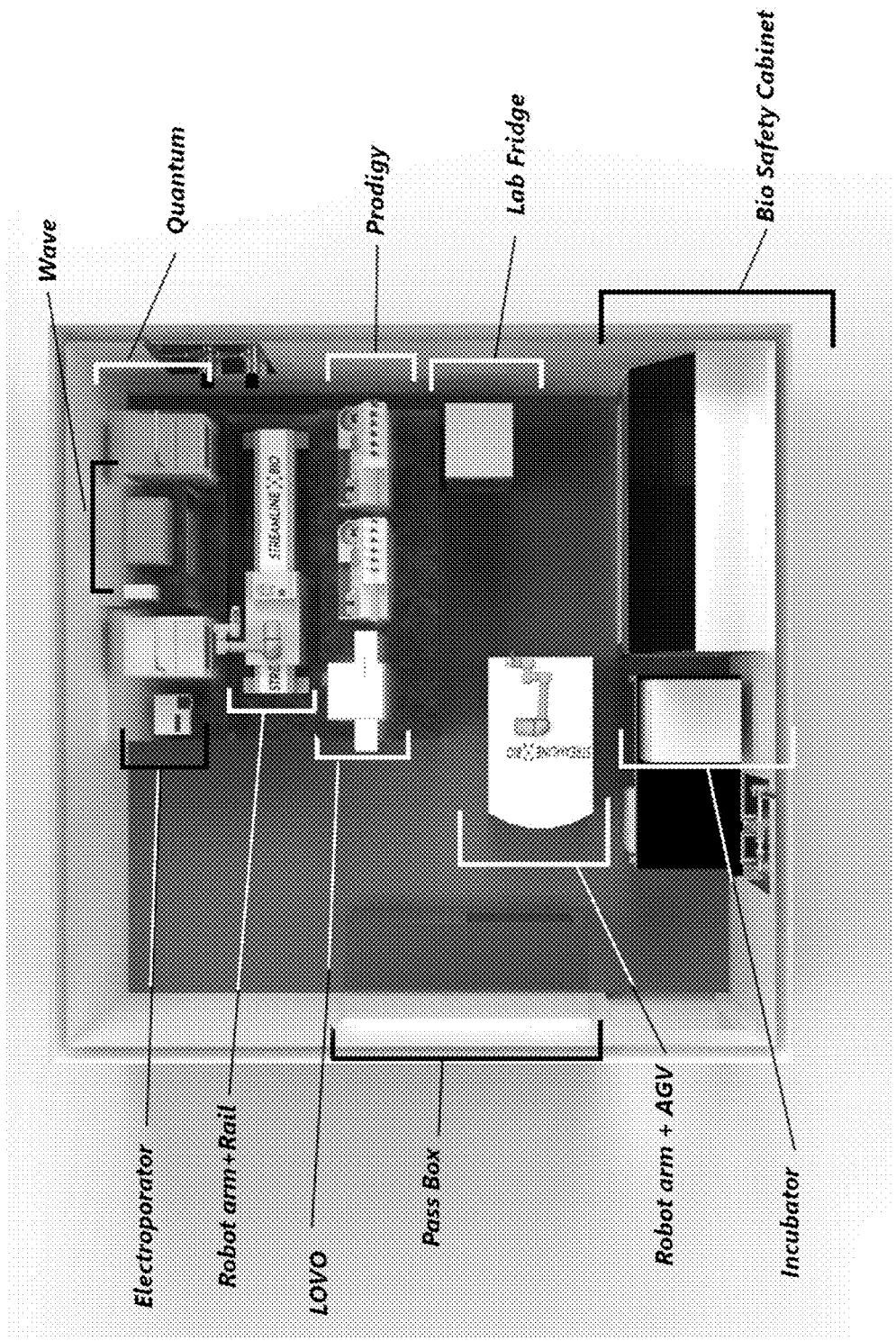
FIG. 3 illustrates an example artificial intelligence (AI)-based laboratory system that is at least substantially automated in some embodiments.

FIG. 3 illustrates an example artificial intelligence-based laboratory system that is at least substantially automated in some embodiments. Referring to FIG. 3, the artificial intelligence robotics system can be a substantially true plug-and-play. With computerized vision, the moving device as a robotic arm in FIG. 3 can perceive the surroundings or the environment by processing sensor data (e.g., camera, Lidar, Radar). The moving device recognizes the bioprocessing machines and contact points to perform unit operations in a predefined sequence.

In some embodiments, the moving device based on artificial intelligence can localize a given object and complete the unit operation, such as fetching an object in different orientations or positions, which can be applicable to localization in general. For example, in some embodiments, a cell culture machine or each contact point to complete unit operations can be localized.

In some embodiments, a moving device can include various types of mechanical structures and related control mechanism. For example, in some embodiments, a moving device may include a robotics-based structure such as a robotic arm. In some embodiments, the robotic arm can be UR 5e. In some embodiments, the robotic arm can have an attaching member which may include an attaching structure module. In some embodiments, an attaching structure module can be in various shapes and structures, such as a cube shape. In some embodiments, the robotic arm can move an object with a precise control.

Figure 4:
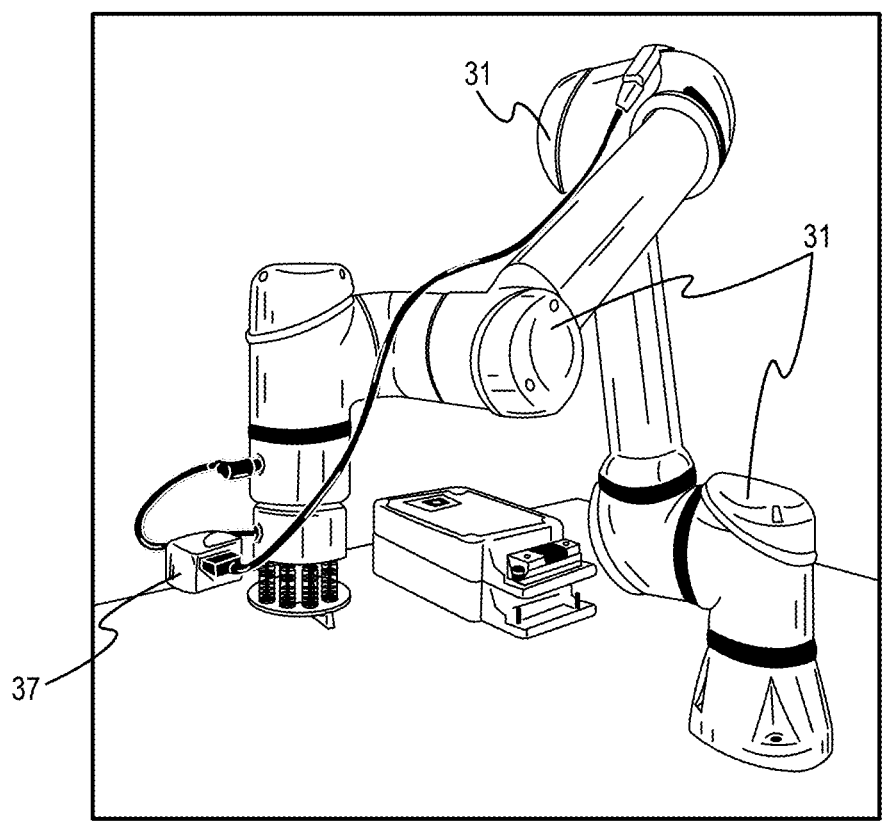
FIG. 4 illustrates an aspect of an example robotic arm as a moving device in some embodiments.

For example, FIG. 4 illustrates an aspect of an example robotic arm 30 as a moving device 30 in some embodiments. Referring to FIG. 4, in some embodiments, the robotic arm 30 may include a plurality of joints 31 to allow a different degree of freedom of motion. In some embodiments, the robotic arm 30 has at least two degrees of freedom. In some embodiments, the robotic arm 30 has at least three degrees of freedom. In some embodiments, the robotic arm 30 has at least four degrees of freedom. In some embodiments, the robotic arm 30 has at least five degrees of freedom. In some embodiments, the robotic arm 30 has at least six degrees of freedom. In some embodiments, the robotic arm 30 has at least seven degrees of freedom. In some embodiments, the robotic arm 30 has at least eight degrees of freedom. In some embodiments, the robotic arm 30 has at least nine degrees of freedom. In some embodiments, the robotic arm 30 has at least ten degrees of freedom.

In some embodiments, the robotic arm 30 can include a sensor 37, which could be selected from a various types of sensors, such as a camera. For example, in some embodiments, as a sensor 37, different types of cameras, such as 2D camera or 3D camera can be used. In some embodiments, various types of sensors can be implemented, such as a camera, LiDAR, Radar, UV light sensor, Infrared sensor, point cloud sensor, laser scanning sensor, electromagnetic wave scanner, Time-of-Flight (ToF) Sensor, a dual lens camera, a structured-light 3D scanner, etc. In some embodiments, the sensor 37 can obtain various information from the surrounding it is sensing and process the various information for operation of the robotic arm 30. For example, in some embodiments, the sensor 37 can obtain various information from the surrounding it is sensing and process the various information to determine an orientation of an object 11 a distance between the sensor 37 and an object 11.

In some embodiments, the sensor 37 is to obtain various types of information such as written codes, indicators, or characteristics and appearance of a physical object or matter. For example, the sensor 37 may obtain information from a solid, liquid, or gas. In some embodiments, the information can include color, temperature, pH, oxygenation status, or any combination thereof. In some embodiments, the information can comprise a computer-readable indicator, and the sensor can read information from the computer-readable indicator. In some embodiments, the computer-readable indicator may include a computer readable code. In some embodiments, the computer readable code can include bar code or a QR code. In some embodiments, the information from the computer-readable indicator is to be processed to determine an orientation of an object.

In some embodiments, the multiple workstations include a patient tissue processing station. In some embodiments, the multiple workstations include a cell enrichment station. In some embodiments, the multiple workstations include a cell activation and/or cell transduction station. In some embodiments, the multiple workstations include a cell proliferation or expansion station. In some embodiments, the multiple workstations include a cell enrichment station. In some embodiments, the multiple workstations include a cell purification and formulation station. In some embodiments, the multiple workstations includes a cell cryopreservation station.

In some embodiments, a manufacturing process for a cell therapy product can be categorized into a pre-process process, a selection process, a non-genetic manipulation process of gene expression, a gene modification process, an expansion process, a harvest process, a formulation of filling process, and a preservation process.

In some embodiments, in a pre-process process, cell therapy products can be derived from human tissues, including peripheral blood, certain organs, connective tissue, bone marrow, dental pulp, umbilical cord, amniotic fluid, placenta, and umbilical cord blood. Because human tissues contain a mixture of various cell types and extracellular matrix (ECM), initial tissues require a preliminary processing step to remove most unwanted cell types and ECM. Depending on the clinical administration strategy for different cell therapy products, if short-term storage of the pre-processed starting material is necessary, the processed starting materials need to undergo cryopreservation and be stored in the vapor phase of liquid nitrogen. In some embodiments, outcomes of a pre-process process may include generating a standardized, homogeneous starting material derived from human tissues, optimized for efficient downstream cell therapy manufacturing. In some embodiments, critical quality attributes (CQAs) can include safety, impurity, identity, quantity, etc. In some embodiments, a pre-process process can include homogenization, isolation, washing, removal, depletion, separation, filtration, pre-treatment, enzymatic treatment, selection, cryopreservation, etc.

In some embodiments, in a selection process, to guarantee that a desirably high purity of the target cell type is utilized during production, the starting materials undergo a critical selection process before manufacturing begins. This step is vital as it significantly increases the proportion of target cells in the starting materials while eliminating unwanted cell types. By ensuring higher purity of the starting materials, the selection process not only enhances the efficiency of the product manufacturing process but also plays a crucial role in the overall success of the therapy. This selection step is especially important for genetically modified cell products, where the precision and purity of the cell population directly impact the efficacy and safety of the final therapeutic product. Ensuring the correct cell type is selected is fundamental to achieving the desired therapeutic outcomes in cell therapy. In some embodiments, outcomes of a selection process may include enhancing the purity of the target cell population while minimizing the proportion of unwanted cell types. In some embodiments, critical quality attributes (CQAs) can include impurity, identity, quantity, potency, etc. In some embodiments, a selection process can include enrichment, isolation, separation, purification, collection, sorting, cumulating, capture, depletion, removal, separation, etc.

In some embodiments, in a non-genetic manipulation of gene expression process, some cell types require priming or pre-conditioning to prepare them for further processing or to improve their quality and function. Common priming or pre-conditioning methods include using cytokines, alloantigens, recombinant proteins, small molecule drugs, or culturing cells under hypoxic conditions. This step is crucial for enhancing the effectiveness and quality of the final cell therapy product. Additionally, gene expression in target cells can be modulated without altering their DNA. Non-genetic methods such as epigenetic control, mRNA, minicircle DNA, and pre-conditioning techniques can adjust gene activity, optimizing cells for therapeutic purposes without involving direct genetic engineering. In some embodiments, outcomes of a non-genetic manipulation of gene expression process may include modulating target cell properties through optimized culture conditions, without genetic modification, to prepare them for subsequent manipulation. In some embodiments, critical quality attributes (CQAs) can include impurity, identity, quantity, potency, etc. In some embodiments, a non-genetic manipulation of gene expression process can include activation, stimulation, enhancing, promotion, booster, seeding, inoculation, recovery, attachment, etc.

In some embodiments, gene modification in cell therapy involves altering the genetic material of cells to boost their therapeutic potential. This approach is often used to provide cells with new or enhanced capabilities to treat diseases, especially when their natural functions are inadequate for effective therapy. The two most common forms of gene modification are gene editing, which precisely alters existing DNA sequences, and the insertion of target DNA sequences to introduce new functions or correct genetic defects In some embodiments, outcomes of a gene modification process may include modulating the expression of one or more genes of the target cells, either permanently or transiently, using biotechnology. In some embodiments, critical quality attributes (CQAs) can include safety, identify, potency, etc. In some embodiments, a gene modification process can include transduction, electroporation, nucleofection, transfection, modification, delivery, genetic engineering, genetic editing, cell squeezing, infusion, microinjection, cargo loading, etc.

In some embodiments, in an expansion process, to produce a sufficient quantity of cell therapy products, an ex vivo expansion process lasting approximately 5 to 30 days is necessary. The culture medium used is carefully selected based on the specific type of cells being expanded, and the timing for replacing or supplementing the medium is adjusted according to the metabolic needs of the cells. In some embodiments, outcomes of an expansion process may include increasing the absolute number of the target cell type. In some embodiments, critical quality attributes (CQAs) can include quantity, identity, etc. In some embodiments, an expansion process can include proliferation, culture, production, growth, etc.

In some embodiments, in a harvest process, after ex vivo expansion, the cells are collected, and non-cellular impurities are removed. For adherent cells, enzymatic treatment is used to detach them from the surface of culture vessels. The harvested cells can either be directly formulated or cryopreserved in liquid nitrogen for future use. In some embodiments, outcomes of a harvest process may include isolating and purifying the target cell type, removing impurities, for subsequent storage or formulation. In some embodiments, critical quality attributes (CQAs) can include safety, impurity, identity, quantity, etc. in some embodiments, a harvest process can include washing, removal, sorting, collection, selection, filtration, etc.

In some embodiments, in a formulation and filling process, For clinical applications and to ensure cell viability, cell products must be reconstituted in an appropriate excipient before administration. The volume and cell concentration used during administration can significantly impact therapeutic efficacy. Therefore, during the excipient addition process, the cell concentration is carefully adjusted to the optimal range. For cell therapy products intended for long-term transport or temporary storage, a cryoprotectant is used as the excipient, and the formulated product is stored in the vapor phase of liquid nitrogen. In some embodiments, outcomes of a formulation and filling process may include that the target cell type is aliquoted into its final dosage form for administration to patients. In some embodiments, critical quality attributes (CQAs) can include safety, impurity, potency, etc. In some embodiments, a formulation and filling process can include reconstitution, concentration, aliquot, etc.

In some embodiments, in a preservation process such as a cryopreservation, some cell therapy products are designed for long-distance transportation or long-term storage. After the harvesting process is completed, these products undergo a controlled-rate freezing procedure. This ensures that the cells freeze with minimal impact on their viability, and they are then stored in the vapor phase of liquid nitrogen. Certain cell types do not require formulation and filling into clinical application containers. Instead, they can be thawed and injected directly into patients. In these situations, the cryopreservation and formulation steps are combined into a single step. In some embodiments, outcomes of a preservation process such as a cryopreservation may include that the target cell type is stably preserved in an appropriate cryoprotectant. In some embodiments, critical quality attributes (CQAs) can include safety, impurity, potency, etc. In some embodiments, a preservation process such as a cryopreservation can include frozen specimens.

The present disclosure relates to robotics data and machine learning that can be used to train a machine learning algorithm, and any type of patient data and surgical robotics data known in the relevant art, such as described herein, can be used. In some embodiments, additional parameters can include profiles, such as the radius, angle and longitudinal position of an object. This can be combined with real time imaging from a sensor for a moving device. In some embodiments, images can be processed with image segmentation, for example, to determine a location of an object or its structure. In some embodiments, artificial intelligence software instructions can be configured to automatically identify the structures and different devices and components and determine the relative locations of each. The data can be vectorized and input into the machine learning classifier, for example.

In some embodiments, moving devices for laboratory work and tasks often necessitate the coordination of multiple mechanical arms during the liquid preparation process. However, the intricate movement trajectories of these arms frequently lead to collisions and other complications, resulting in a cumbersome experimental process, elevated costs, and a low level of automation.

The present disclosure is related to robotics data and machine learning that can be used to train a machine learning algorithm, and any type of data and robotics data as described herein can be used. In some embodiments, this can be combined with sensor data such as imaging including real time imaging from the imaging devices. In some embodiments, the images may comprise a portion of the laboratory platform described herein. In some embodiments, the images can be processed with image segmentation, for example, to determine the location of an object. The artificial intelligence software instructions can be configured to automatically identify structure or arrangements of different equipment or objects. The data can be vectorized and input into the machine learning classifier, for example.

In some embodiments, devices, kits, systems and methods disclosed herein may comprise a sensor or detector such as a plurality of sensors, each of which is capable of measuring and recording states of various systems and objects such as the robotic system components, which can be used for analysis to improve the automated procedures and outcomes. For example, the robotics system may comprise a plurality of parameters related to the state of the system and associated components, such as an angle of a shaft, a longitudinal position of a shaft, data related to energy used to an object, real time imaging for example. In some embodiments, data during a process can be recorded in real time and used to generate a plurality of data frames corresponding to the state of the robotics system throughout the process. The data frames may correspond to fixed time intervals between frames, e.g. one second, in order to provide input data suitable for processing with machine learning or artificial intelligence as described herein.

In some embodiments, input data can be generated and recorded from or for many types of systems. The presently disclosed methods and apparatus are well suited for combination with many applications related to robotics, and can incorporate the hardware, processors and software of many prior systems.

In some embodiments, the processor, controller and control electronics and circuitry can include one or more of many suitable components, such as one or more processor, one or more field-programmable gate array (FPGA), and one or more memory storage devices. In many embodiments, the control electronics controls the control panel of the graphic user interface (hereinafter "GUI") to provide for, for example, a process planning.

In some embodiments, the sensor data, position data, and recorded treatment positions may comprise any of the sensor data, position data, and recorded treatment positions as described herein. The recorded data may comprise data of locations, status, and various properties, the light source, the arm lock, the arm controller, the linkage, each of the angle sensors, the patient support, or the base, for example.

In some embodiments, The data may comprise priming data, docking data, angle data, scale data, calibration data, cut profile data, corresponding times of one or more of these, and planned treatment time, for example.

In some embodiments, the data can be modified with the artificial intelligence or machine learning as described herein.

A method of locating and moving an object can be provided in some embodiments, such as those involving artificial intelligence, machine training or deep learning. While the method can be performed in many ways, in some embodiments, the robotics data comprises a plurality of parameters recorded during the process, a process time, a set up time, an imaging time, a time a sensor moves and reads, a plurality of locations and orientations of an object and robotic arm, a plurality of images FIG. 5 illustrates an example method of operations of a moving device for locating and manipulating an object in some embodiments.

Figure 5:
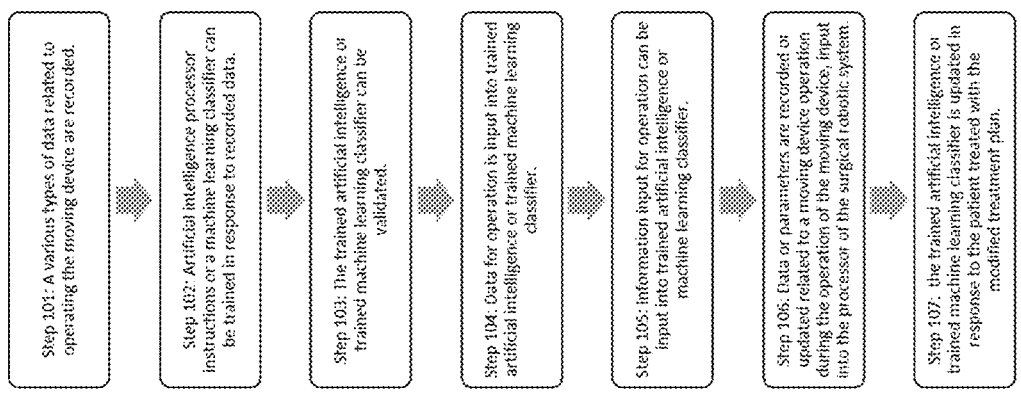
FIG. 5 illustrates an example method of operations of a moving device for locating and manipulating an object in some embodiments.

Referring to FIG. 5, at a step 101 a various types of data related to operating the moving device such as location coordinates and different parameters such as temperature are recorded. For example, in some movements, set up data related to the process or operation of robotic arm can be recorded. In some embodiments, different statuses, conditions, or parameters of the process such as a cell culture can be recorded. In some embodiments, sensor data and data related to one or more robotic components can be recorded. In some embodiments, the data corresponding to each of the plurality of images can be recorded. In some embodiments, data frames can be generated from various types of data, such as the plurality of images and sensor data and other operating data. In some embodiments, the data frames may comprise image frames corresponding to fixed intervals, such as one second between frames. In some embodiments, Alternatively or in combination vectorized data can be generated from the image frames.

At a step 102, artificial intelligence processor instructions or a machine learning classifier can be trained in response to recorded data such as data in step 101. In some embodiments, artificial intelligence processor instructions may comprise one or more of machine learning, search and mathematical optimization, artificial neural networks, statistics, probability, support vector machine learning, clustering of data groups, image classification, image segmentation. In some embodiments, the machine learning processor instructions may comprise one or more of decision tree learning, association rule learning, artificial neural networks, deep learning, inductive logic programming, support vector machines, clustering, Bayesian networks, reinforcement learning, representation learning, similarity and metric learning, sparse dictionary learning, genetic algorithms, rule based machine learning or a learning classifier system.

At a step 103 the trained artificial intelligence or trained machine learning classifier can be validated.

At a step 104 data for operation is input into trained artificial intelligence or trained machine learning classifier.

At a step 105 information input for operation can be input into trained artificial intelligence or machine learning classifier.

At a step 106 data or parameters are recorded or updated related to a moving device operation during the operation of the moving device, input into the processor of the surgical robotic system.

At a step 107 the trained artificial intelligence or trained machine learning classifier is updated in response to data or parameters that are recorded or updated.

One or more steps of the artificial intelligence-based method may be performed with circuitry or processor instructions as described herein, for example, one or more of a processor or a logic circuitry of the systems described herein. The circuitry may be programmed to provide one or more steps 101 through 107, and the program may comprise program instructions stored on a computer readable memory or programmed steps of the logic circuitry such as with programmable array logic or a field programmable gate array, for example.

In some embodiments, an example method of operations of a moving device may include environment scanning and 3D model creation. In some embodiments, sensors such as LiDAR, depth cameras, standard cameras, and radar can be used to scan the cleanroom or facility. In some embodiments, sensor data (e.g., point clouds) can be processed using computer vision techniques. In some embodiments, a comprehensive 3D model of the environment can be built.

In some embodiments, an example method of operations of a moving device may include CAD/simulation software integration. In some embodiments, the 3D model can be into CAD/simulation software, and using the CAD/simulation software automation equipment, sensors, control units, actuators, and accessories in the simulated environment can be arranged, for example, to create a relatively accurate digital representation of the physical space.

In some embodiments, an example method of operations of a moving device may include reality check and fine-tuning. For example, in some embodiments, the simulated environment may be with the real-world space, e.g., to identify and correct any discrepancies or refine the digital model for more accuracy or precision.

In some embodiments, an example method of operations of a moving device may include advanced simulation environment setup. For example, the refined 3D model can be imported into advanced simulators like Isaac Sim or similar real-world simulators. In some embodiments, these platforms can be used to design the overall workflow of the automation system.

In some embodiments, an example method of operations of a moving device may include physics property configuration. For example, physical properties for at least some of all objects in the simulated environment can be set, which may include dynamic/static attributes, mass, force, torque, elasticity, etc., to ensure accurate representation of real-world physics.

In some embodiments, an example method of operations of a moving device may include workflow design. For example, end-to-end sequences for client's products may be designed and unit operations for at least some or all objects (machines, consumables, products), can be defined. In some embodiments, detailed process flows within the simulation can be created.

In some embodiments, an example method of operations of a moving device may include artificial intelligence (AI) motion planning. For example, the movement of the robotic system with AI algorithms can be designed. For instance, AI motion planning algorithms can be used to generate detailed waypoints on how each of the joints of a robotic arm would move to operate each of the unit operations.

In some embodiments, an example method of operations of a moving device may include initial real-world deployment. For example, the simulated workflow in the actual cleanroom environment can be deployed and the initial setup and identify any discrepancies can be tested.

In some embodiments, an example method of operations of a moving device may include iterative refinement. For example, any of the aforementioned embodiments in an example method of operations of a moving device can be repeated for the iterative refinement, e.g., to continuously refine the simulation and real-world setup, or to iterate until the process is stable and smooth in both environments.

In some embodiments, an example method of operations of a moving device may include visual checkpoint implementation. For example, visual checkpoints (e.g., AprilTags) for object localization can be added, which can be used, e.g., to compensate for positional and orientational errors, to ensure precise functionality of equipment, sensors, and actuators In some embodiments, an example method of operations of a moving device may include automation program export. For example, the automation program script from the simulation can be generated and exported. The script for implementation in the real-world system can be prepared.

In some embodiments, an example method of operations of a moving device may include final workflow verification. For example, the exported program in the real environment can be run and the workflow process and results can be thoroughly checked. Final adjustments can be as necessary In some embodiments, an example method of operations of a moving device may include continuous monitoring and optimization. For example, ongoing monitoring of the real-world system can be implemented. The digital twin can be updated to reflect any changes. The digital twin for future optimizations and expansions can be used.

Figure 6:
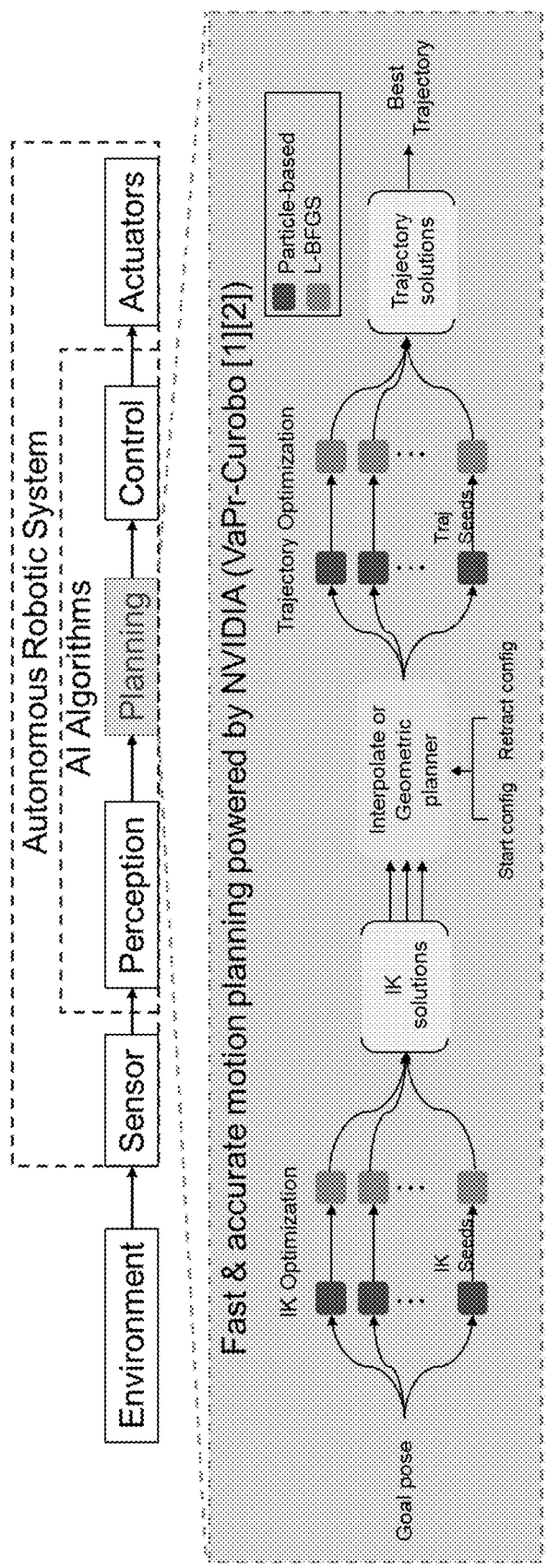
FIG. 6 shows an example autonomous robotics system flow chart in some embodiments.

For example, FIG. 6 shows an example autonomous robotics system flow chart in some embodiments. Referring to FIG. 6, to enable full simulation in a digital twin simulator, steps according to any of the foregoing embodiments can be implemented, including building 3D modules for each object and enabling the physical movement for each dynamic object.

In some embodiments, digital-twin and AI enabled plug and play robotic system can be implemented. In some embodiments, the complete design flow features of digital twin simulation and AI decision making pipeline to enable a flexible and customizable plug-and-play autonomous robotic system can be implemented. In some embodiments, according to the present disclosure, a substantially true plug-and-play, interoperable system that can be incorporated into any existing production line. For example, AI empowered plug-and-play feature may allow a moving device such as a robotic arm to move between interfaced machines in a smart and fast fashion based on simulation in a digital twin, e.g., a digital twin powered by NVIDIA. In some embodiments, interoperable modular feature, e.g., a precision robotics according to the present disclosure can mimic human operators' actual movements so it can operate substantially most and all the machines on the production line. In some embodiments, AI algorithm according to the present disclosure can be custom-built to accommodate the complicated biomanufacturing environment.

In some embodiments, the platforms, systems, media, and methods described herein may include a digital processing device, or use of the same. In some embodiments, the digital processing device includes one or more hardware central processing units (CPUs) or general purpose graphics processing units (GPGPUs) that carry out the device's functions. In some embodiments, the digital processing device may further comprise an operating system configured to perform executable instructions. In some embodiments, the digital processing device is optionally connected a computer network. In further embodiments, the digital processing device is optionally connected to the Internet such that it accesses the World Wide Web. In still further embodiments, the digital processing device is optionally connected to a cloud computing infrastructure. In other embodiments, the digital processing device is optionally connected to an intranet. In other embodiments, the digital processing device is optionally connected to a data storage device.

In accordance with the description herein, suitable digital processing devices include, by way of non-limiting examples, server computers, desktop computers, laptop computers, notebook computers, sub-notebook computers, netbook computers, netpad computers, set-top computers, media streaming devices, handheld computers, Internet appliances, mobile smartphones, tablet computers, personal digital assistants, video game consoles, and vehicles. Those of skill in the art will recognize that many smartphones are suitable for use in the system described herein. Those of skill in the art will also recognize that select televisions, video players, and digital music players with optional computer network connectivity are suitable for use in the system described herein. Suitable tablet computers include those with booklet, slate, and convertible configurations, known to those of skill in the art.

In some embodiments, the digital processing device includes an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWareR. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing. Those of skill in the art will also recognize that suitable mobile smart phone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, and Palm® WebOS®. Those of skill in the art will also recognize that suitable media streaming device operating systems include, by way of non-limiting examples, Apple TV®, Roku®, Boxee®, Google TV®, Google Chromecast®, Amazon Fire®, and Samsung® HomeSync®. Those of skill in the art will also recognize that suitable video game console operating systems include, by way of non-limiting examples, SonyR PS3®, Sony® PS4®, Microsoft® Xbox 360®, Microsoft Xbox One, Nintendo® Wii®, Nintendo® Wii U®, and Ouya®.

In some embodiments, the device includes a storage and/or memory device. The storage and/or memory device is one or more physical apparatuses used to store data or programs on a temporary or permanent basis. In some embodiments, the device is volatile memory and requires power to maintain stored information. In some embodiments, the device is non-volatile memory and retains stored information when the digital processing device is not powered. In further embodiments, the non-volatile memory comprises flash memory. In some embodiments, the non-volatile memory comprises dynamic random-access memory (DRAM). In some embodiments, the non-volatile memory comprises ferroelectric random access memory (FRAM). In some embodiments, the non-volatile memory comprises phase-change random access memory (PRAM). In other embodiments, the device is a storage device including, by way of non-limiting examples, CD-ROMs, DVDs, flash memory devices, magnetic disk drives, magnetic tape drives, optical disk drives, and cloud computing based storage. In further embodiments, the storage and/or memory device is a combination of devices such as those disclosed herein.

In some embodiments, the digital processing device includes a display to send visual information to a user. In some embodiments, the display is a cathode ray tube (CRT). In some embodiments, the display is a liquid crystal display (LCD). In further embodiments, the display is a thin film transistor liquid crystal display (TFT-LCD). In some embodiments, the display is an organic light emitting diode (OLED) display. In various further embodiments, on OLED display is a passive-matrix OLED (PMOLED) or active-matrix OLED (AMOLED) display. In some embodiments, the display is a plasma display. In other embodiments, the display is a video projector. In still further embodiments, the display is a combination of devices such as those disclosed herein.

In some embodiments, the digital processing device includes an input device to receive information from a user. In some embodiments, the input device is a keyboard. In some embodiments, the input device is a pointing device including, by way of non-limiting examples, a mouse, trackball, track pad, joystick, game controller, or stylus. In some embodiments, the input device is a touch screen or a multi-touch screen. In other embodiments, the input device is a microphone to capture voice or other sound input. In other embodiments, the input device is a video camera or other sensor to capture motion or visual input. In further embodiments, the input device is a Kinect, Leap Motion, or the like. In still further embodiments, the input device is a combination of devices such as those disclosed herein.

Figure 7:
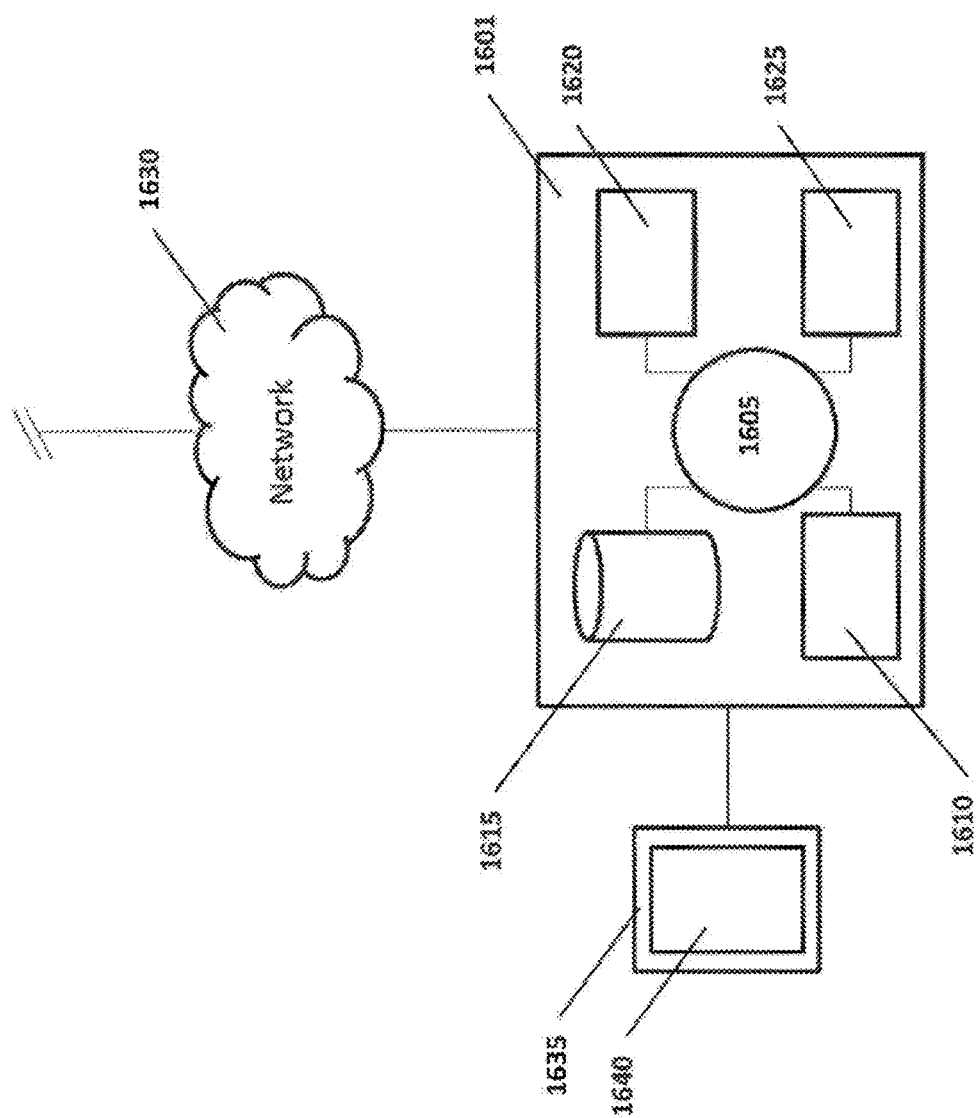
FIG. 7 illustrates a processor system, in accordance with some embodiments.

For example, FIG. 7 illustrates a processor system, in accordance with some embodiments.

Referring to FIG. 7, in a particular embodiment, an exemplary digital processing device 1601 is programmed or otherwise configured to use artificial intelligence or machine learning to set up, plan or perform a surgical robotics procedure. The device 1601 can regulate various aspects of the machine learning and artificial intelligence of the present disclosure, such as, for example, determination of a cut profile in response to data of a patient to be treated and data from previously treated patients and previous surgical procedures as described herein. In this embodiment, the digital processing device 1601 includes a central processing unit (CPU, also "processor" and "computer processor" herein) 1605, which can be a single core or multi core processor, or a plurality of processors for parallel processing. The digital processing device 1601 also includes memory or memory location 1610 (e.g., random-access memory, read-only memory, flash memory), electronic storage unit 1615 (e.g., hard disk), communication interface 1620 (e.g., network adapter) for communicating with one or more other systems, and peripheral devices 1625, such as cache, other memory, data storage and/or electronic display adapters. The memory 1610, storage unit 1615, interface 1620 and peripheral devices 1625 are in communication with the CPU 1605 through a communication bus (solid lines), such as a motherboard. The storage unit 1615 can be a data storage unit (or data repository) for storing data. The digital processing device 1601 can be operatively coupled to a computer network ("network") 1630 with the aid of the communication interface 1620. The network 1630 can be the Internet, an internet and/or extranet, or an intranet and/or extranet that is in communication with the Internet. The network 1630 in some cases is a telecommunication and/or data network. The network 1630 can include one or more computer servers, which can enable distributed computing, such as cloud computing. The network 1630, in some cases with the aid of the device 1601, can implement a peer-to-peer network, which may enable devices coupled to the device 1601 to behave as a client or a server.

Continuing to refer to FIG. 7, the CPU 1605 can execute a sequence of machine-readable instructions, which can be embodied in a program or software. The instructions may be stored in a memory location, such as the memory 1610. The instructions can be directed to the CPU 1605, which can subsequently program or otherwise configure the CPU 1605 to implement methods of the present disclosure. Examples of operations performed by the CPU 1605 can include fetch, decode, execute, and write back. The CPU 1605 can be part of a circuit, such as an integrated circuit. One or more other components of the device 1601 can be included in the circuit. In some cases, the circuit is an application specific integrated circuit (ASIC) or a field programmable gate array (FPGA).

Continuing to refer to FIG. 7, the storage unit 1615 can store files, such as drivers, libraries and saved programs. The storage unit 1615 can store user data, e.g., user preferences and user programs. The digital processing device 1601 in some cases can include one or more additional data storage units that are external, such as located on a remote server that is in communication through an intranet or the Internet.

Continuing to refer to FIG. 7, the digital processing device 1601 can communicate with one or more remote computer systems through the network 1630. For instance, the device 1601 can communicate with a remote computer system of a user. Examples of remote computer systems include personal computers (e.g., portable PC), slate or tablet PCs (e.g., Apple® iPad, Samsung® Galaxy Tab), telephones, Smart phones (e.g., Apple® iPhone, Android-enabled device, Blackberry®), or personal digital assistants.

Methods as described herein can be implemented by way of machine (e.g., computer processor) executable code stored on an electronic storage location of the digital processing device 1601, such as, for example, on the memory 1610 or electronic storage unit 1615. The machine executable or machine readable code can be provided in the form of software. During use, the code can be executed by the processor 1605. In some cases, the code can be retrieved from the storage unit 1615 and stored on the memory 1610 for ready access by the processor 1605. In some situations, the electronic storage unit 1615 can be precluded, and machine-executable instructions are stored on memory 1610.

In some embodiments, the platforms, systems, media, and methods disclosed herein include one or more non-transitory computer readable storage media encoded with a program including instructions executable by the operating system of an optionally networked digital processing device. In further embodiments, a computer readable storage medium is a tangible component of a digital processing device. In still further embodiments, a computer readable storage medium is optionally removable from a digital processing device. In some embodiments, a computer readable storage medium includes, by way of non-limiting examples, CD-ROMs, DVDs, flash memory devices, solid state memory, magnetic disk drives, magnetic tape drives, optical disk drives, cloud computing systems and services, and the like. In some cases, the program and instructions are permanently, substantially permanently, semi-permanently, or non-transitorily encoded on the media.

In some embodiments, the platforms, systems, media, and methods disclosed herein include at least one computer program, or use of the same. A computer program includes a sequence of instructions, executable in the digital processing device's CPU, written to perform a specified task. Computer readable instructions may be implemented as program modules, such as functions, objects, Application Programming Interfaces (APIs), data structures, and the like, that perform particular tasks or implement particular abstract data types. In light of the disclosure provided herein, those of skill in the art will recognize that a computer program may be written in various versions of various languages.

The functionality of the computer readable instructions may be combined or distributed as desired in various environments. In some embodiments, a computer program comprises one sequence of instructions. In some embodiments, a computer program comprises a plurality of sequences of instructions. In some embodiments, a computer program is provided from one location. In other embodiments, a computer program is provided from a plurality of locations. In various embodiments, a computer program includes one or more software modules. In various embodiments, a computer program includes, in part or in whole, one or more web applications, one or more mobile applications, one or more standalone applications, one or more web browser plug-ins, extensions, add-ins, or add-ons, or combinations thereof.

In some embodiments, a computer program includes a web application. In light of the disclosure provided herein, those of skill in the art will recognize that a web application, in various embodiments, utilizes one or more software frameworks and one or more database systems. In some embodiments, a web application is created upon a software framework such as Microsoft® .NET or Ruby on Rails (RoR). In some embodiments, a web application utilizes one or more database systems including, by way of non-limiting examples, relational, non-relational, object oriented, associative, and XML database systems. In further embodiments, suitable relational database systems include, by way of non-limiting examples, Microsoft® SQL Server, mySQL™, and Oracle®. Those of skill in the art will also recognize that a web application, in various embodiments, is written in one or more versions of one or more languages. A web application may be written in one or more markup languages, presentation definition languages, client-side scripting languages, server-side coding languages, database query languages, or combinations thereof. In some embodiments, a web application is written to some extent in a markup language such as Hypertext Markup Language (HTML), Extensible Hypertext Markup Language (XHTML), or extensible Markup Language (XML). In some embodiments, a web application is written to some extent in a presentation definition language such as Cascading Style Sheets (CSS). In some embodiments, a web application is written to some extent in a client-side scripting language such as Asynchronous Javascript and XML (AJAX), Flash® Actionscript, Javascript, or Silverlight®. In some embodiments, a web application is written to some extent in a server-side coding language such as Active Server Pages (ASP), ColdFusion®, Perl, Java™, JavaServer Pages (JSP), Hypertext Preprocessor (PHP), Python™, Ruby, Tcl, Smalltalk, WebDNA®, or Groovy. In some embodiments, a web application is written to some extent in a database query language such as Structured Query Language (SQL). In some embodiments, a web application integrates enterprise server products such as IBM® Lotus Domino®. In some embodiments, a web application includes a media player element. In various further embodiments, a media player element utilizes one or more of many suitable multimedia technologies including, by way of non-limiting examples, Adobe® Flash®, HTML 5, Apple® QuickTime®, Microsoft® Silverlight®, Java™, and Unity®.

In some embodiments, a computer program includes a mobile application provided to a mobile digital processing device. In some embodiments, the mobile application is provided to a mobile digital processing device at the time it is manufactured. In other embodiments, the mobile application is provided to a mobile digital processing device via the computer network described herein.

In view of the disclosure provided herein, a mobile application is created by techniques known to those of skill in the art using hardware, languages, and development environments known to the art. Those of skill in the art will recognize that mobile applications are written in several languages. Suitable programming languages include, by way of non-limiting examples, C, C++, C#, Objective-C, Java™, Javascript, Pascal, Object Pascal, Python™, Ruby, VB.NET, WML, and XHTML/HTML with or without CSS, or combinations thereof.

Suitable mobile application development environments are available from several sources. Commercially available development environments include, by way of non-limiting examples, AirplaySDK, alcheMo, Appcelerator®, Celsius, Bedrock, Flash Lite, .NET Compact Framework, Rhomobile, and WorkLight Mobile Platform. Other development environments are available without cost including, by way of non-limiting examples, Lazarus, MobiFlex, MoSync, and Phonegap. Also, mobile device manufacturers distribute software developer kits including, by way of non-limiting examples, iPhone and iPad (iOS) SDK, Android™ SDK, BlackBerry® SDK, BREW SDK, Palm® OS SDK, Symbian SDK, webOS SDK, and Windows® Mobile SDK.

Those of skill in the art will recognize that several commercial forums are available for distribution of mobile applications including, by way of non-limiting examples, Apple® App Store, Google® Play, Chrome WebStore, BlackBerry® App World, App Store for Palm devices, App Catalog for webOS, Windows® Marketplace for Mobile, Ovi Store for Nokia® devices, Samsung® Apps, and Nintendo® DSi Shop.

In some embodiments, a computer program includes a standalone application, which is a program that is run as an independent computer process, not an add-on to an existing process, e.g., not a plug-in. Those of skill in the art will recognize that standalone applications are often compiled. A compiler is a computer program(s) that transforms source code written in a programming language into binary object code such as assembly language or machine code. Suitable compiled programming languages include, by way of non-limiting examples, C, C++, Objective-C, COBOL, Delphi, Eiffel, Java™, Lisp, Python™, Visual Basic, and VB .NET, or combinations thereof. Compilation is often performed, at least in part, to create an executable program. In some embodiments, a computer program includes one or more executable complied applications.

In some embodiments, the computer program includes a web browser plug-in (e.g., extension, etc.). In computing, a plug-in is one or more software components that add specific functionality to a larger software application. Makers of software applications support plug-ins to enable third-party developers to create abilities which extend an application, to support easily adding new features, and to reduce the size of an application. When supported, plug-ins enable customizing the functionality of a software application. For example, plug-ins are commonly used in web browsers to play video, generate interactivity, scan for viruses, and display particular file types. Those of skill in the art will be familiar with several web browser plug-ins including, Adobe® Flash® Player, Microsoft® Silverlight®, and Apple® QuickTime®. In some embodiments, the toolbar comprises one or more web browser extensions, add-ins, or add-ons. In some embodiments, the toolbar comprises one or more explorer bars, tool bands, or desk bands.

In view of the disclosure provided herein, those of skill in the art will recognize that several plug-in frameworks are available that enable development of plug-ins in various programming languages, including, by way of non-limiting examples, C++, Delphi, Java™ PHP, Python™, and VB .NET, or combinations thereof.

Web browsers (also called Internet browsers) are software applications, designed for use with network-connected digital processing devices, for retrieving, presenting, and traversing information resources on the World Wide Web. Suitable web browsers include, by way of non-limiting examples, Microsoft® Internet Explorer®, Mozilla® Firefox®, Google® Chrome, Apple® Safari®, Opera Software® Opera®, and KDE Konqueror. In some embodiments, the web browser is a mobile web browser. Mobile web browsers (also called mircrobrowsers, mini-browsers, and wireless browsers) are designed for use on mobile digital processing devices including, by way of non-limiting examples, handheld computers, tablet computers, netbook computers, subnotebook computers, smartphones, music players, personal digital assistants (PDAs), and handheld video game systems. Suitable mobile web browsers include, by way of non-limiting examples, Google® Android® browser, RIM Blackberry® Browser, Apple® Safari®, Palm® Blazer, Palm® WebOS® Browser, Mozilla® Firefox® for mobile, Microsoft® Internet Explorer® Mobile, Amazon® Kindle® Basic Web, Nokia® Browser, Opera Software® Opera® Mobile, and Sony® PSP™ browser.

In some embodiments, the platforms, systems, media, and methods disclosed herein include software, server, and/or database modules, or use of the same. In view of the disclosure provided herein, software modules are created by techniques known to those of skill in the art using machines, software, and languages known to the art. The software modules disclosed herein are implemented in a multitude of ways. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application.

In some embodiments, software modules are hosted on one machine. In other embodiments, software modules are hosted on more than one machine. In further embodiments, software modules are hosted on cloud computing platforms. In some embodiments, software modules are hosted on one or more machines in one location. In other embodiments, software modules are hosted on one or more machines in more than one location.

In some embodiments, the platforms, systems, media, and methods disclosed herein include one or more databases, or use of the same. In view of the disclosure provided herein, those of skill in the art will recognize that many databases are suitable for storage and retrieval of patient information and surgical information as described herein. In various embodiments, suitable databases include, by way of non-limiting examples, relational databases, non-relational databases, object oriented databases, object databases, entity-relationship model databases, associative databases, and XML databases. Further non-limiting examples include SQL, PostgreSQL, MySQL, Oracle, DB2, and Sybase. In some embodiments, a database is internet-based. In further embodiments, a database is web-based. In still further embodiments, a database is cloud computing-based.

In some embodiments, the user select data to use with a selected algorithm, for example. This can allow the user to consider outcome likelihood odds and risks for differing scenarios and with a desired outcome versus risk, for example.

The user interface 1700 may comprise a user input 1760 for the user to select parameters of the model used to determine the values of the one or more of the safety and efficacy parameters as disclosed herein. This selection of the parameters can allow the user to pick parameters that may be more helpful than others, and to remove parameters that may be less helpful than others for a particular patient. For example, if a user believes that a parameter such as age is less helpful for predicting outcomes, the user can deselect that parameter as input to the classifier model used to predict the outcome. Alternatively, if the user believes that age is a helpful parameter, the user can select age as a parameter to be used as input to the classifier model.

The user interface 1700 may comprise a user input 1770 for the user to select data to be shown on the display. The data shown on the display may comprise visualization data for example. In some embodiments, the user can select whether to show a suggested treatment profile on the display overlaid with the planned treatment profile the patient after user adjustment. This can be helpful to the user to determine how far the planned treatment profile for the patient deviates from the profile suggested by the algorithm. The user can select additional types of visualization data to be shown on the display. For example, the user can select a planned trajectory of the energy source for the treatment.

NON-LIMITING EMBODIMENTS

The following Examples are detailed by way of illustration only and are not to be construed as limiting in spirit or in scope, many modifications both in materials and in methods will be apparent to those skilled in the art.

1. A system comprising:
   a lab space housing multiple workstations comprising at least two workstations each performing a different type of bio lab task from another,
   wherein the lab space has a lab floor space comprising an occupied lab floor space on which the multiple workstations are occupied, and an unoccupied lab floor space on which a stand-alone robotic arm moves through,
   wherein the stand-alone robotic arm comprises visual assistance to determine a move path on the unoccupied lab floor space for the stand-alone robotic arm to move to or among the multiple workstations, and wherein the visual assistance assists the stand-alone robotic arm to be positioned at each of the multiple workstations depending on the bio lab task to be performed.
2. The system of Embodiment 1, wherein the stand-alone robotic arm is not attached to any of the multiple workstations.
3. The system of Embodiment 1-2, wherein the lab floor space does not include a track on which robotic arm moves.
4. The system of Embodiment 1-2, wherein the lab floor space includes a track on which robotic arm moves.
5. The system of Embodiment 1-4, wherein the visual assistance visualizes the path and modify the path depending on the relative positions of the multiple workstations.
6. The system of Embodiment 1-5, wherein the visual assistance visualizes the path and modify the path depending on the shapes of the multiple workstations.
7. The system of Embodiment 1-6, wherein the visual assistance visualizes the path and modify the path depending on the relative positions of obstacles unrelated to the multiple workstations.
8. The system of Embodiment 1-7, wherein no more than about 80% of the lab floor space is unoccupied.
9. The system of Embodiment 1-7, wherein no more than about 75% of the lab floor space is unoccupied.
10. The system of Embodiment 1-7, wherein no more than about 70% of the lab floor space is unoccupied.
11. The system of Embodiment 1-7, wherein no more than about 65% of the lab floor space is unoccupied.
12. The system of Embodiment 1-7, wherein no more than about 60% of the lab floor space is unoccupied.
13. The system of Embodiment 1-7, wherein no more than about 55% of the lab floor space is unoccupied.
14. The system of Embodiment 1-7, wherein no more than about 50% of the lab floor space is unoccupied.
15. The system of Embodiment 1-7, wherein no more than about 45% of the lab floor space is unoccupied.
16. The system of Embodiment 1-7, wherein no more than about 40% of the lab floor space is unoccupied.
17. The system of Embodiment 1-7, wherein no more than about 35% of the lab floor space is unoccupied.
18. The system of Embodiment 1-7, wherein no more than about 30% of the lab floor space is unoccupied.
19. The system of Embodiment 1-7, wherein no more than about 25% of the lab floor space is unoccupied.
20. The system of Embodiment 1-7, wherein no more than about 20% of the lab floor space is unoccupied.
21. The system of Embodiment 1-7, wherein no more than about 15% of the lab floor space is unoccupied.
22. The system of Embodiment 1-7, wherein no more than about 10% of the lab floor space is unoccupied.
23. The system of Embodiment 1-7, wherein no more than about 5% of the lab floor space is unoccupied.
24. The system of Embodiment 1-23, wherein the stand-alone robotic arm includes a controller that controls the movement of the stand-alone robotic arm to perform tasks on multiple workstations, and wherein visualization assistance is operationally associated with the controller to assist the stand-alone robotic arm to perform tasks.
25. The system of Embodiment 1-24, wherein visualization assistance visualizes a functional object on the workstation and assists the stand-alone robotic arm to move toward and manipulate the functional object.
26. The system of Embodiment 1-24, wherein visualization assistance visualizes a functional object on the workstation and assists the stand-alone robotic arm to grab the functional object.
27. The system of Embodiment 1-24, wherein visualization assistance visualizes a functional object on the workstation and assists the stand-alone robotic arm to contact the functional object.
28. The system of Embodiment 1-24, wherein visualization assistance visualizes a functional object on the workstation and assists the stand-alone robotic arm to transfer the functional object from one location to another location.
29. The system of Embodiment 1-24, wherein visualization assistance visualizes a functional object on the workstation and assists the stand-alone robotic arm to rub the functional object.
30. The system of Embodiment 1-24, wherein visualization assistance visualizes a functional object on the workstation and assists the stand-alone robotic arm to actuate a switch on the functional object.
31. The system of Embodiment 1-24, wherein visualization assistance visualizes a functional object on the workstation and assists the stand-alone robotic arm to push a button on a functional object.
32. The system of Embodiment 1-24, wherein visualization assistance visualizes a functional object on the workstation and assists the stand-alone robotic arm to touch a touch screen.
33. The system of Embodiment 1-24, wherein the stand-alone robotic arm includes a controller that controls the movement of the stand-alone robotic arm to perform tasks on multiple workstations, and wherein visualization assistance is operationally associated with the controller to assist the stand-alone robotic arm to move toward and manipulate the functional object.
34. The system of Embodiment 1-24, wherein the stand-alone robotic arm includes a controller that controls the movement of the stand-alone robotic arm to perform tasks on multiple workstations, and wherein visualization assistance is operationally associated with the controller to assist the stand-alone robotic arm to grab the functional object.
35. The system of Embodiment 1-24, wherein the stand-alone robotic arm includes a controller that controls the movement of the stand-alone robotic arm to perform tasks on multiple workstations, and wherein visualization assistance is operationally associated with the controller to assist the stand-alone robotic arm to contact the functional object.
36. The system of Embodiment 1-24, wherein the stand-alone robotic arm includes a controller that controls the movement of the stand-alone robotic arm to perform tasks on multiple workstations, and wherein visualization assistance is operationally associated with the controller to assist the stand-alone robotic arm to transfer the functional object from one location to another location.
37. The system of Embodiment 1-24, wherein the stand-alone robotic arm includes a controller that controls the movement of the stand-alone robotic arm to perform tasks on multiple workstations, and wherein visualization assistance is operationally associated with the controller to assist the stand-alone robotic arm to rub the functional object.
38. The system of Embodiment 1-24, wherein the stand-alone robotic arm includes a controller that controls the movement of the stand-alone robotic arm to perform tasks on multiple workstations, and wherein visualization assistance is operationally associated with the controller to assist the stand-alone robotic arm to actuate a switch on the functional object.
39. The system of Embodiment 1-24, wherein the stand-alone robotic arm includes a controller that controls the movement of the stand-alone robotic arm to perform tasks on multiple workstations, and wherein visualization assistance is operationally associated with the controller to assist the stand-alone robotic arm to push a button on a functional object.
40. The system of Embodiment 1-24, wherein the stand-alone robotic arm includes a controller that controls the movement of the stand-alone robotic arm to perform tasks on multiple workstations, and wherein visualization assistance is operationally associated with the controller to assist the stand-alone robotic arm to touch a touch screen.
41. The system of Embodiment 1-40, wherein the visualization assistance further visualizes the failure of moving toward the functional object and inform the controller to adjust the movement of the stand-alone robotic arm.
42. The system of Embodiment 24-41, wherein the visualization assistance further visualizes a failure of manipulating the functional object and inform the controller to adjust the movement of the stand-alone robotic arm to adjust manipulating the functional object.
43. The system of Embodiment 24-41, wherein the visualization assistance further visualizes an obstructing object obstructing the stand-alone robotic arm from manipulating the functional object and inform the controller to adjust the movement of the stand-alone robotic arm to adjust manipulating the functional object.
44. The system of Embodiment 24-41, wherein the visualization assistance further visualizes a failure of going around an object and inform the controller to adjust the movement of the stand-alone robotic arm to adjust manipulating the functional object.
45. The system of Embodiment 24-41, wherein the visualization assistance further visualizes a failure of manipulating the functional object and inform the controller to adjust the movement of the stand-alone robotic arm to adjust manipulating the functional object.
46. The system of Embodiment 24-41, wherein the visualization assistance further visualizes a failure of grabbing the functional object and inform the controller to adjust the movement of the stand-alone robotic arm to adjust grabbing the functional object.
47. The system of Embodiment 24-41, wherein the visualization assistance further visualizes a failure of contacting the functional object and inform the controller to adjust the movement of the stand-alone robotic arm to adjust contacting the functional object.
48. The system of Embodiment 24-41, wherein the visualization assistance further visualizes a failure of transferring the functional object from one location to another and inform the controller to adjust the movement of the stand-alone robotic arm to adjust transferring the functional object.
49. The system of Embodiment 24-41, wherein the visualization assistance further visualizes a failure of rubbing the functional object and inform the controller to adjust the movement of the stand-alone robotic arm to adjust rubbing the functional object.
50. The system of Embodiment 24-41, wherein the visualization assistance further visualizes a failure of actuating the switch on the functional object and inform the controller to adjust the movement of the stand-alone robotic arm to adjust actuating the switch the functional object.
51. The system of Embodiment 24-41, wherein the visualization assistance further visualizes a failure of touching the touch screen from one location to another and inform the controller to adjust the movement of the stand-alone robotic arm to adjust touching the touch screen.
52. The system of Embodiment 24-51, wherein the visualization assistance comprises a sensor.
53. The system of Embodiment 24-51, wherein the visualization assistance comprises a 3D sensor.
54. The system of Embodiment 24-51, wherein the visualization assistance comprises a camera.
55. The system of Embodiment 24-51, wherein the visualization assistance comprises a 3D camera.
56. The system of Embodiment 24-51, wherein the visualization assistance comprises a LiDAR sensor.
57. The system of Embodiment 24-51, wherein the visualization assistance comprises a laser sensor.
58. The system of Embodiment 24-51, wherein the visualization assistance comprises a UV light sensor.
59. The system of Embodiment 24-51, wherein the visualization assistance comprises an infrared sensor.
60. The system of Embodiment 24-51, wherein the visualization assistance comprises a point cloud sensor.
61. The system of Embodiment 24-51, wherein the visualization assistance comprises a laser scanning sensor.
62. The system of Embodiment 24-51, wherein the visualization assistance comprises an electromagnetic wave scanner.
63. The system of Embodiment 24-51, wherein the visualization assistance comprises a Time-of-Flight (ToF) Sensor.
64. The system of Embodiment 24-51, wherein the visualization assistance comprises a Dual lens camera.
65. The system of Embodiment 24-51, wherein the visualization assistance comprises a structured-light 3D scanner.
66. The system of Embodiment 1-65, wherein the multiple workstations comprise a patient tissue processing station.
67. The system of Embodiment 1-65, wherein the multiple workstations comprise a cell enrichment station.
68. The system of Embodiment 1-65, wherein the multiple workstations comprise a cell activation and/or cell transduction station.
69. The system of Embodiment 1-65, wherein the multiple workstations comprise a cell proliferation or expansion station.
70. The system of Embodiment 1-65, wherein the multiple workstations comprise a cell enrichment station.
71. The system of Embodiment 1-65, wherein the multiple workstations comprise a cell purification and formulation station.
72. The system of Embodiment 1-65, wherein the multiple workstations comprises a cell cryopreservation station.
73. The system of Embodiment 1-72, wherein the system operates based on a computer-implemented method comprising:

obtaining a three dimensional map of a bio lab environment;
assigning locations of the multiple workstations for interactions by the stand-alone robotic arm;
generating a plurality of waypoints corresponding to the multiple workstations, using a machine learning model and based on the three dimensional map of the bio lab environment and the locations of the multiple workstations the interaction point;
generating operation data from monitoring operation of the robotic device to control the multiple workstations operated based on the plurality of waypoints; and
feeding back the generated operation data to the machine learning model to generate an updated plurality of waypoints corresponding to the multiple workstations.

Of note, the exemplar embodiments of the disclosure described herein do not limit the scope of the invention since these embodiments can be merely examples of the embodiments of the invention. Any equivalent embodiments can be intended to be within the scope of this invention. Indeed, various modifications of the disclosure, in addition to those shown and described herein, such as alternative useful combinations of the elements described, may become apparent to those skilled in the art from the description. Such modifications and embodiments can be also intended to fall within the scope of the appended claims.

What is claimed is:

1. A system comprising:
a lab space housing multiple workstations comprising at least two workstations respectively performing bio lab tasks different from another,
wherein the lab space has a lab floor space comprising an occupied lab floor space on which the multiple workstations are occupied, and an unoccupied lab floor space on which a stand-alone robotic arm moves through, wherein no more than about 40% of the lab floor space is unoccupied
wherein the stand-alone robotic arm comprises visual assistance configured to generate visual data associated with at least partial visualization of the multiple workstations and at least partial visualization of the unoccupied lab floor space for the stand-alone robotic arm to move to or among the multiple workstations,
wherein the system includes at least one hardware processor configured to control the movement of the stand-alone robotic arm using an iterative refinement algorithm configured to continuously adjust the movement after a failure to perform a bio lab task associated with a functional object on a workstation among the multiple workstations by processing the visual data,
wherein the visual assistance is operationally associated with the at least one hardware processor and is to generate the visual data to be processed the at least one hardware processor to generate a move path on the unoccupied lab floor space the stand-alone robotic arm to move along to be positioned at each of the multiple workstations using the iterative refinement algorithm depending on a different type of the bio lab tasks to be performed.

2. The system of claim 1, wherein the stand-alone robotic arm is not attached to any of the multiple workstations.

3. The system of claim 1, wherein the visual assistance visualizes the path and modify the path depending on relative positions or shapes of the multiple workstations.

4. The system of claim 1, wherein no more than about 30% of the lab floor space is unoccupied.

5. The system of claim 1, wherein no more than about 25% of the lab floor space is unoccupied.

6. The system of claim 1, wherein the visual assistance visualizes the functional object on the workstation and assists the stand-alone robotic arm to move toward and manipulate the functional object.

7. The system of claim 1, wherein the visual assistance visualizes the functional object on the workstation and assists the stand-alone robotic arm to contact the functional object.

8. The system of claim 1, wherein the stand-alone robotic arm includes at least one hardware processor that controls the movement of the stand-alone robotic arm to perform tasks on multiple workstations, and wherein the visual assistance is operationally associated with the at least one hardware processor to assist the stand-alone robotic arm to move toward and manipulate the functional object.

9. The system of claim 1, wherein the stand-alone robotic arm includes at least one hardware processor that controls the movement of the stand-alone robotic arm to perform tasks on multiple workstations, and wherein the visual assistance is operationally associated with the at least one hardware processor to assist the stand-alone robotic arm to contact the functional object.

10. The system of claim 1, wherein the visual assistance further visualizes the failure of moving toward the functional object and inform the at least one hardware processor to adjust the movement of the stand-alone robotic arm.

11. The system of claim 1, wherein the visual assistance further visualizes a failure of manipulating the functional object and inform the at least one hardware processor to adjust the movement of the stand-alone robotic arm to adjust manipulating the functional object.

12. The system of claim 1, wherein the visual assistance further visualizes a failure of going around an object and inform the at least one hardware processor to adjust the movement of the stand-alone robotic arm to adjust manipulating the functional object.

13. The system of claim 1, wherein the visual assistance further visualizes a failure of manipulating the functional object and inform the at least one hardware processor to adjust the movement of the stand-alone robotic arm to adjust manipulating the functional object.

14. The system of claim 1, wherein the visual assistance further visualizes a failure of contacting the functional object and inform the at least one hardware processor to adjust the movement of the stand-alone robotic arm to adjust contacting the functional object.

15. The system of claim 1, wherein the visual assistance further visualizes a failure of actuating a switch on the functional object and inform the at least one hardware processor to adjust the movement of the stand-alone robotic arm to adjust actuating the switch the functional object.

16. The system of claim 1, wherein the visual assistance further visualizes a failure of touching a touch screen from one location to another and inform the at least one hardware processor to adjust the movement of the stand-alone robotic arm to adjust touching the touch screen.

17. The system of claim 1, wherein the visual assistance comprises a sensor.

18. The system of claim 1, wherein the multiple workstations comprise a patient tissue processing station, a cell enrichment station, a cell activation or cell transduction station, a cell proliferation or expansion station, a cell enrichment station, a cell purification and formulation station, a cell cryopreservation station, or a combination thereof.

19. The system of claim 1, wherein the operation executed by the at least one hardware processor comprises a computer-implemented method comprising:
- obtaining a three dimensional map of a bio lab environment;
- assigning locations of the multiple workstations for interactions by the stand-alone robotic arm;
- generating a plurality of waypoints corresponding to the multiple workstations, using a machine learning model and based on the three dimensional map of the bio lab environment and the locations of the multiple workstations;
- generating, by the at least one hardware processor, the operation data from monitoring operation of the robotic arm to control the multiple workstations operated based on the plurality of waypoints and the visual assistance; and
- feeding, by the at least one hardware processor, back the generated operation data to the machine learning model executed by the at least one hardware processor to retrain the machine learning model, to generate an updated plurality of waypoints corresponding to the multiple workstations using the retrained the machine learning model.

* * * * *